US010829546B2

(12) United States Patent
Depicker et al.

(10) Patent No.: US 10,829,546 B2
(45) Date of Patent: Nov. 10, 2020

(54) PROTECTIVE ANTI-ETEC ANTIBODY

(71) Applicants: VIB VZW, Ghent (BE); Universiteit Gent, Ghent (BE); Vrije Universiteit Brussel, Brussels (BE)

(72) Inventors: Anna Depicker, Schelderode (BE); Henri De Greve, Brussels (BE); Vikram Virdi, Ghent (BE)

(73) Assignees: VIB VZW, Ghent (BE); Universiteit Gent, Ghent (BE); Vrije Universiteit Brussel, Brussels (BE)

( * ) Notice: Subject to any disclaimer, the term of this patent is extended or adjusted under 35 U.S.C. 154(b) by 346 days.

(21) Appl. No.: 14/425,606

(22) PCT Filed: Sep. 3, 2013

(86) PCT No.: PCT/EP2013/068152
§ 371 (c)(1),
(2) Date: Mar. 3, 2015

(87) PCT Pub. No.: WO2014/033313
PCT Pub. Date: Mar. 6, 2014

(65) Prior Publication Data
US 2015/0252100 A1 Sep. 10, 2015

(30) Foreign Application Priority Data
Sep. 3, 2012 (EP) .................................... 12182774

(51) Int. Cl.
*C07K 16/12* (2006.01)
*C07K 16/46* (2006.01)
*A23K 20/147* (2016.01)
*A23L 33/185* (2016.01)
*A61K 39/00* (2006.01)

(52) U.S. Cl.
CPC ........ *C07K 16/1232* (2013.01); *A23K 20/147* (2016.05); *A23L 33/185* (2016.08); *C07K 16/462* (2013.01); *A23V 2002/00* (2013.01); *A61K 2039/505* (2013.01); *C07K 2317/13* (2013.01); *C07K 2317/22* (2013.01); *C07K 2317/24* (2013.01); *C07K 2317/522* (2013.01); *C07K 2317/569* (2013.01); *C07K 2317/76* (2013.01); *C07K 2319/00* (2013.01)

(58) Field of Classification Search
None
See application file for complete search history.

(56) References Cited

U.S. PATENT DOCUMENTS

| 2009/0087478 | A1* | 4/2009 | Hansen | C07K 16/1282 424/450 |
| 2012/0269842 | A1* | 10/2012 | Zhang | A61K 31/195 424/190.1 |
| 2015/0252100 | A1* | 9/2015 | De Picker | C07K 16/1232 424/133.1 |
| 2016/0280795 | A1* | 9/2016 | Wang | C07K 16/2809 |

FOREIGN PATENT DOCUMENTS

| WO | 2004048606 A2 | 6/2004 |
| WO | 2004074491 A2 | 9/2004 |
| WO | 2007010040 A1 | 1/2007 |
| WO | 2014033313 A1 | 3/2014 |

OTHER PUBLICATIONS

McCue, BioProcess International, Feb. 2010. Novel Affinity Ligands Provide for Highly Selective Primary Capture. 4 pages (Year: 2010).*
DeBuck et al, Plant Biotechnology Journal, 2013, 11:1006-1016, (Year: 2013).*
Garaicoechea et al, Journal of Virology, Oct. 2008, 82/19:9753-9764, published ahead ff print on Jul. 16, 2008 (Year: 2008).*
Joosten et al, Microbial Cell Factories, 2003, 2:, 15 pages. published Jan. 30, 2003 (Year: 2003).*
Muda et al, Protein Engineering, Design & Selection, 2011, 24/5:447-454 (Year: 2011).*
Arbabi-Ghahroudi, Frontiers in Immunology, Nov. 2017, vol. 8, Article 1589. 8 pages. published: Nov. 20, 2017 (Year: 2017).*
Fernandes et al, Frontiers in Immunology, Jun. 2017, vol. 8, Article 653, 8 pages, published: Jun. 9, 2017 (Year: 2017).*
Harmsen et al, Appl. Microbiol. Biotechnol. 2006, 72:544-554. published online: Feb. 1, 2006 (Year: 2006).*
Harmsen et al, Veterinary Microbiology, 2005, 111:89-98 (Year: 2005).*
Hybribody by Hybrigenics Services, 2016. VHH Antibody Properties, 3 pages. (Year: 2016).*
Kolkman et al, Drug Discovery Today: Technologies, 2010, vol. 7, No. 2, e139-e146 (Year: 2010).*
Maass et al. Journal of Immunological Methods, 2007, 324"13-25. available online: May 15, 2007 (Year: 2007).*
Moonens et al, PLoS ONE 2014, 9/12:e0114691, 20 pages, published: Dec. 11, 2014 (Year: 2014).*
Moonens et al, Veterinary Research, 2015, 46:14, 7 pages. (Year: 2015).*
Muyldermans, Reviews in Molecular Biotechnology, 2001, 74:277-302. (Year: 2001).*
Nguyen et al, The EMBO Journal, 2000, 19/5:921-930 (Year: 2000).*

(Continued)

*Primary Examiner* — Nita M. Minnifield
(74) *Attorney, Agent, or Firm* — Patent Law Works LLP

(57) ABSTRACT

This disclosure relates to an antibody that can protect against ETEC infection in a passive immunization set up. More specifically, it relates to a VHH grafted on an IgA scaffold and produced in plant seeds. When the seeds are given in food or feed, the subject is protected against ETEC infection.

11 Claims, 15 Drawing Sheets
Specification includes a Sequence Listing.

(56) References Cited

OTHER PUBLICATIONS

Steeland et al, Drug Discovery Today, Jul. 2016 (Year: 2016).*
Virdi et al, PNAS, USA. Jul. 16, 2013, vol. 110, No. 29, pp. 11809-11814. (Year: 2013).*
Virdi et al, Nature Biotechnology, May 2019, 37:527-530. https://doi.org/10.1038/s41587-019-0070-x (Year: 2019).*
Virdi et al, Fron. Immunol. Conference Abstract: ECMIS-*E. coli* and the Mucosal Immune System: Interaction, Modualtion and Vaccination.Jul. 2-Jul. 5, 2011. Abstract only (Year: 2011).*
Harmsen et al., *Escherichia coli* F4 fimbriae specific llama single-domain antibody fragments effectively inhibit bacterial adhesion in vitro but poorly protect against diarrhoea, Vet Microbiol., 2005, pp. 89-98, vol. 111.
Harmsen et al., Prolonged in vivo residence times of llama single-domain antibody fragments in pigs by binding to porcine immunoglobulins, Vaccine, Sep. 30, 2005, pp. 4926-4934, vol. 23, No. 41, Elsevier Ltd, GB.
De Geus et al., Prevention of diarrhoea using pathogen specific monoclonal antibodies in an experimental enterotoxigenic *E-coli* infection in germfree piglets, Vet Q., Jun. 3, 1998, pp. S87-S89, vol. 20, No. S3.
Yokoyama et al., Passive protective effect of chicken egg yolk immunoglobulins against experimental enterotoxigenic *Escherichia coli* infection in neonatal piglets, Infect Immun., Mar. 1, 1992, pp. 998-1007, vol. 60.
PCT International Search Report, PCT/EP2013/068152, dated Dec. 3, 2013.
Eyer, L., and K. Hruska. "Single-Domain Antibody Fragments Derived from Heavy-Chain Antibodies: a Review." VeterinÃ¡RnÃ-MedicÃ-Na, vol. 57, No. No. 9, 2012, pp. 439-513., doi:10.17221/6336-vetmed.

* cited by examiner

| plant line | % of T2 seeds | % of homozygous T3 seeds |
|---|---|---|
| mV1A18 | 0,49 | n.d. |
| mV1CA28 | 0,49 | 0,51 |
| mV1cA 38 | 0,55 | 0,54 |
| mV2A17 | 0,58 | n.d. |
| mV3A 38 | 0,58 | 0,71 |
| mV3A 51 | 0,68 | n.d. |
| mV3A29 | n.d. | 0,75 |
| mV4A 30 | 0,59 | n.d. |
| mV4A 36 | 0,76 | n.d. |
| mV4A 4 | n.d. | 0,74 |
| dV2A14 | 0,52 | 0,74 |
| dV3A8 | 0,46 | n.d. |
| dV1cA27 | 0,68 | 0,88 |
| dv2A42 | 0,62 | 0,68 |
| sV2A8 | 0,45 | 0,53 |
| sV3A40 | 0,53 | 0,51 |

FIG. 9A

PROTECTIVE ANTI-ETEC ANTIBODY

CROSS-REFERENCE TO RELATED APPLICATIONS

This application is a national phase entry under 35 U.S.C. § 371 of International Patent Application PCT/EP2013/068152, filed Sep. 3, 2013, designating the United States of America and published in English as International Patent Publication WO 2014/033313 A1 on Mar. 6, 2014, which claims the benefit under Article 8 of the Patent Cooperation Treaty and under 35 U.S.C. § 119(e) to European Patent Application Serial No. 12182774.5, filed Sep. 3, 2012, the disclosure of each of which is hereby incorporated herein in its entirety by this reference.

TECHNICAL FIELD

This disclosure relates to an antibody that can protect against ETEC infection in a passive immunization set up. More specifically, it relates to a VHH grafted on an IgA scaffold and produced in plant seeds. When the seeds are given in food or feed, the subject is protected against ETEC infection.

BACKGROUND

One of the most important causes of economic loss to the global porcine rearing industry is post-weaning diarrhea (PWD) (Amezcua et al., 2002; Hong et al., 2006). PWD in piglets is regarded as a multifactorial disease, caused by the overwhelming conglomeration of physical, physiological and psychological stress at weaning that makes the piglets vulnerable to pathogens like enterotoxigenic *E. coli* (ETEC), especially F4-positive enterotoxigenic *E. coli* (F4+ETEC) (Madec et al., 2000) and F18-positive enterotoxigenic *E. coli* (F18+ETEC). The F4 and F18 fimbriae serve both as virulence markers and virulence factors (Fairbrother et al., 2005). The protective immunity provided by maternal milk antibodies during suckling period is discontinued at weaning (Riising et al., 2005; Wilson and Svendsen, 1971), and as a consequence, in addition to the looming stress, piglets succumb to infections caused by F4+ETEC and/or F18+ETEC. In theory, this protection can be prolonged by oral administration of antibodies after weaning (Marquardt et al., 1999; Niewold et al., 2007; Yokoyama et al., 1992).

De Geus et al. (1998) showed partial protection (only during the administration of the antibody) using a monoclonal IgG-type antibody against $F4_{ac}$ fimbriae in an experimental ETEC infection in neonatal germfree piglets. However, possible protection was only noted during the administration of the antibody. Moreover, their experiments were biased by the presence or absence of the $F4_{ac}$ receptor in the piglets, and no significant difference in protection could be seen between the agglutinating anti-$F4_{ac}$ antibodies and the non-agglutinating control antibody during the whole experiment.

Apart from the lack of activity, there is the high production cost of classical monoclonal antibodies. To reduce the production cost, Harmsen et al. (2005) isolated VHHs against F4⁺ETEC bacteria, intended for oral passive immunization, with the understanding that VHHs are robust antibody fragments that can be produced at a low cost. In spite of the group's promising in vitro results, the VHH passive immunotherapy failed to offer any protection in vivo. The authors attributed this failure, amongst others, to proteolysis of VHH in the gastrointestinal tract. Indeed, oral passive immunization as a route for passive protection is only guaranteed by antibodies that can withstand and be functional in the harsh gastric environment (Reilly et al., 1997). Harmsen et al. (2005) suggested producing bivalent structures as one of the possible strategies to increase the efficacy of the immune therapy, but there is no evidence that this approach could work, as lack of avidity is only one of the possible causes of the failure.

There are several methods for creating bivalent VHH structures (for a review, see Vanlandschoot et al., 2011). Bivalent and multivalent VHHs can be constructed by multimerization of the VHH domain. Alternatively, dimerization of the VHHs is obtained by fusing the VHH to a (heterologous) Fc chain, mimicking the camelid heavy chain or even the classical antibody structure. Heterologous VHH-Fc fusions have been described, amongst others, in U.S. 2007/0237769 and by Aliprandi et al. (2010). However, such constructs have never been tested in the treatment of ETEC.

In order to reduce the production cost of recombinant antibodies, the antibodies or antibody fragment can be produced in plants. WO 2004/074491 describes the production in plants of antibodies with specificity against ETEC, and the use of these plants to treat ETEC. WO 2007/010040 discloses how a scFv single chain antibody against bacterial F4 fimbriae can be produced in plants or microorganisms and the use of these plants as fodder for mammals. However, the protective effect in vivo of these IgG antibodies against ETEC challenge was not demonstrated or hardly significant. In theory, antibodies produced in seed and given as food or feed are protected by bio-encapsulation (Khan et al., 2012). However, to be functional, they need to be released from the feed matrix. This functionality has not been proven yet and needs to be experimentally evaluated.

There is still a need for a robust anti-ETEC antibody design, capable of being produced in plants, wherein the antibody gives sufficient protection against bacterial challenge, when the plants or plant parts are used as feed.

DISCLOSURE

Surprisingly, it was found that antibodies against F4+ETEC, designed by fusion of the llama heavy chain variable fragment to porcine IgA Fc and produced in *Arabidopsis* seeds could prevent F4+ETEC binding to gut villous enterocytes in vitro. Even more surprisingly, the anti-ETEC VHH-IgA fusion polypeptide showed good protection against ETEC infection in an in vivo challenge. The seed-produced antibodies survived the gastric canal and were biologically functional in the intestine. The seed-produced antibodies were leading to rapid clearance of challenge bacterial strain from the piglet system, and prevented F4+ETEC colonization. This protection was clearly superior than the protection obtained with a similar VHH fusion to an IgG domain. In the latter case, some disease symptoms were even aggravated. This effect of the VHH-IgG construct may be due to the neonatal Fc receptor-mediated transcytosis of the disease antigen and cross-linking of bacteria.

The disclosure as presented herein shows the first evidence of effective feed-based oral prophylaxis using IgA-like antibodies.

A first aspect of the disclosure is a fusion protein comprising an anti-ETEC VHH fused to an IgA Fc domain. VHHs are known to the person skilled in the art, and consist of the antigen-binding heavy chain variable domain of a camelid heavy-chain antibody (Vanlandschoot et al., 2011).

In one preferred embodiment, the fusion protein may form a bivalent complex indicated as IgA monomer (mIgA). In another preferred embodiment, two fusion proteins according to the disclosure are linked tail-to-tail, preferably by complex formation with a J chain, to form a tetravalent dimeric IgA (dIgA). In still another preferred embodiment, the dIgA complex is further stabilized, e.g., by the secretory compound of IgA to form secretory IgA-like antibody (sIgA). A schematic representation of the preferred embodiments is given in FIG. 1. Preferably, VHH is directed against an antigen of F4 fimbriae or F18 fimbriae. In one preferred embodiment, VHH is directed against an antigen of F4 fimbriae, preferably it is directed against the FaeG domain, even more preferably, VHH is recognizing the three known serotypes FaeGab, FaeGac and FaeGad. In another preferred embodiment, VHH is directed against an antigen of F18 fimbriae; more preferably it is directed against the FedF lectin domain; and most preferably it is directed against the domain $FedF_{15-165}$. Preferably, the IgA Fc domain is a porcine IgA Fc domain; even more preferably, it is a porcine $IgA^b$ Fc domain.

Another aspect of the disclosure is a nucleic acid encoding a fusion protein according to the disclosure. In a preferred embodiment, the nucleic acid is codon-optimized for plant expression. Preferably, the nucleic acid is placed under control of a promoter, enabling expression in plants or plant cells. Even more preferably, nucleic acid is placed under control of a promoter enabling the expression during seed formation and/or allowing accumulation of the encoded fusion protein in the seeds. Plant-specific promoters, as well as seed-specific promoters, are known to the person skilled in the art. As a non-limiting example, the CaMV 35S promoter can be used as a plant-specific promoter; seed-specific promoters are preferably promoters of genes encoding seed storage proteins, such as Arcelin or Phaseolin promoter. "Accumulation," as used herein, means that the seed comprises at least 0.5% fusion protein (W:W) as calculated on the total soluble protein of the seed; preferably, the seeds comprise at least 1% fusion protein; more preferably, at least 1.5%; even more preferably, at least 2%; even more preferably, at least 2.5%; even more preferably, at least 3%; even more preferably, at least 3.5%; even more preferably, at least 4%; even more preferably, at least 4.5%; and most preferably, at least 5%. Preferably, the nucleic acid comprises a sequence encoding a protein selected from the group consisting of SEQ ID NO:2, SEQ ID NO:4, SEQ ID NO:6 and SEQ ID NO:8. More preferably, the nucleic acid comprises one of the sequences selected from the group consisting of SEQ ID NO:1, SEQ ID NO:3, SEQ ID NO:5 and SEQ ID NO:7. Even more preferably, the nucleic acid consists of a nucleic acid selected from the group consisting of SEQ ID NO:1, SEQ ID NO:3, SEQ ID NO:5 and SEQ ID NO:7.

Still another aspect of the disclosure is a transgenic plant expressing a fusion protein according to the disclosure. Preferably, the expression is combined with the expression of the J chain and/or of the secretory component. Preferably, the nucleic acids encoding the J chain and the secretory component are codon-optimized for seed expression as depicted in SEQ ID NO:9 (J chain) and SEQ ID NO:10 (secretory component). Preferably, the expression is seed specific. The plant can be any plant. Preferably, the plant is suitable for food or feed production. Even more preferably, the plant is a plant with edible seeds, such as, but not limited to, peas, beans such as soybean, or crops such as corn, wheat, barley, sorghum, rice and oat. In a preferred embodiment, the plant is soybean. In another preferred embodiment, the plant is pea.

Still another aspect of the disclosure is the use of a fusion protein according to the disclosure for the manufacture of a medicament for the treatment of an ETEC infection, preferably ETEC-related diarrhea. "ETEC," as used herein, is any enterotoxigenic *Escherichia coli* infection in an animal, preferably in a mammal, including humans. As a non-limiting example, the ETEC infection can be an $F4^+$ *E. coli* or an $F18^+$ *E. coli*. Preferably, the ETEC infection is caused by an $F4^+$ *E. coli*. In a preferred embodiment, the mammal is a pig, preferably a weaned pig. A "medicament," as used herein, can be any medicament known to the person skilled in the art. Preferably, it is an oral medicament. Even more preferably, the medicament is a functional food and/or feed. A "functional food or feed," as used herein, is a fortified, enriched or enhanced food or feed that has a beneficial effect on the health of the subject consuming it when consumed as a part of the diet on a regular basis at effective levels.

Another aspect of the disclosure is a fusion protein for use in treatment of an ETEC infection, as defined above. A preferred use is the use where the fusion protein is incorporated in the food or feed of the infected animal.

Still another aspect of the disclosure is a transgenic plant, comprising a fusion protein according to the disclosure for use in treatment of an ETEC infection. Preferably, the fusion protein according to the disclosure is accumulated in the seeds of the transgenic plant. Preferably, the plant is a plant with edible seeds that are used in food and/or feed. In a preferred embodiment, the transgenic plant seed comprising the fusion protein according to the disclosure is used for the manufacture of a functional food and/or feed for the treatment of an ETEC infection. Preferably, the transgenic plant seed is used as a food or feed additive. Even more preferably, it is used at a concentration of lower than 2% of the total food or feed.

BRIEF DESCRIPTION OF THE FIGURES

FIGS. 9A-9E: Quantification of accumulation of functional IgA units among the sIgA, dIgA and mIgA plant lines. FIG. 9A: The table shows the expression levels of seed produced VHH-IgA in mIgA, dIgA and sIgA lines, determined by making the sum of intensities of the four VHH-IgA bands (37 kDa to 50 kDa) from the respective immunoblots. Immunoblots (FIGS. 9A and 9B) show the T2 and T3 mIgA lines, while FIGS. 9D and 9E show T2 (FIG. 9D) and T3 (FIG. 9E) sIgA and dIgA lines, respectively. It is estimated that only 50% of this total accumulation is functional, i.e., on an average 1% of total soluble protein or 0.2% of seed weight.

DETAILED DESCRIPTION

Examples

Figure 1:
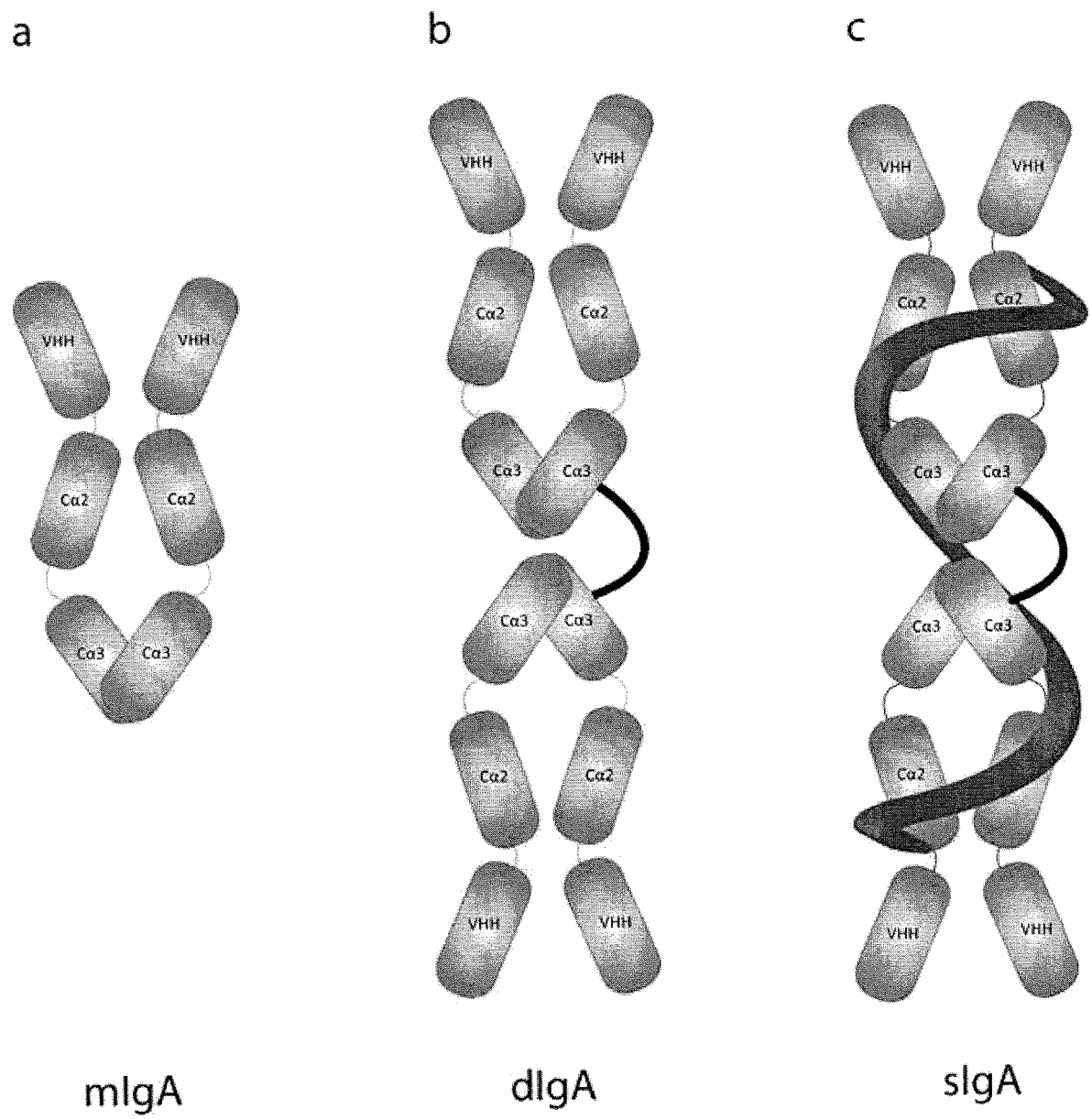
FIG. 1: Schematic representation of the simplified IgA molecules. Column A: The VHH (VHH) is fused to the porcine IgA Fc domain (Cα2-Cα3) with a short hinge to form a divalent IgA monomer (mIgA); Column B: two mIgA bound tail-to-tail by incorporation of a J chain (black) form a tetravalent (4 VHHs) dimeric IgA (dIgA); Column C: a simplified secretory IgA (sIgA) is formed when the secretory component (broad black band) wraps around the dIgA complex. Abbreviations: Cα2, Cα3 are the constant domains of porcine IgA heavy chain.

Example 1: Construction of VHH-IgA and VHH-IgG Fusion Proteins

Purified recombinant FaeGac was used to immunize a healthy llama. The cDNA library construction, phage display and panning procedures were carried out according to the standard procedures. Independent FaeG binding VHHs were selected by ELISA on plates coated with the antigenic variants FaeGac and FaeGad. Colonies corresponding to the VHH giving a positive signal in the ELISA screen were further tested by amplifying the VHH gene. Identical VHHs were eliminated using restriction fragment length polymorphism analysis (RFLP). Finally, four different VHHs were selected and sequenced. Those are indicated as V1, V2, V3 and V4.

In silico, the sequence of the Fc part of the porcine IgA$^b$ (Genbank U12594; version U12594.1, GI:555826) was optimized for expression in plant seeds, and fused at the carboxyterminal end to the DNA sequence of VHH V1. Upstream of the VHH1 initiation codon, the EcoRI restrictions site, the Kozak sequence (CCACC) and the 2S2 seed storage signal peptide sequence were added, while downstream of the Fc coding region, a KDEL endoplasmic retention signal, stop codon and BamHI restriction site were introduced. The entire stretch of DNA, flanked with the GATEWAY® attB1 and attB2 sites was chemically synthesized. The construct was cloned into the multiple cloning site of the pUC57 vector (Genscript). In a GATEWAY® BP reaction, this pUC57 vector, bearing the construct in between the attB sites, was recombined with the GATE- WAY® plasmid pDONR221 (Invitrogen), according to the instructions of the manufacturer. The resulting plasmid was named pEV1A.

For cloning of the other three anti-F4+ETEC VHHs, V2, V3 and V4 in fusion with IgA$^b$ Fc, the DNA sequence for the restriction site for EcoRI+Kozak sequence+2S2 seed storage signal peptide was fused to each of the three VHHs and chemically synthesized. Then, using the EcoRI and the BstEII (located in framework 4 of all VHHs) restriction sites, the VHHs V2, V3 and V4 with the 2S2 signal peptide were swapped with the V1 from entry clone pEV1A. Thus, entry clones (E) pEV2A, pEV3A and pEV4A were made.

The sequence of the fusion constructs is shown in SEQ ID NO:1 through SEQ ID NO:4.

A similar strategy was used to construct the coding sequences for VHH-IgG antibodies. The codon sequence of the porcine IgG3 gene (Genbank EU372658; version EU372658.1; GI:166236036) was retrieved and the sequence of the hinge, CH2 and CH3 regions was codon optimized and, like above, on the 3' end, the KDEL tag and BamHI DNA sequence were added, while upstream of the hinge, the "EcoRI-Kozak-2S2 signal peptide-VHH V1" coding sequence was added and synthesized chemically within the attB1 and attB2 sites. Using the same EcoRI-BstEII-based cloning strategy as described above, the four VHHs were fused to the hinge and Fc fragment of porcine IgG3, resulting in the plasmids pEV1G, pEV2G, pEV3G and pEV4G.

Example 2: Identification and Cloning of the Porcine J Chain

The amino acid sequence of the porcine J chain has not been published. However, given the overall genetic similarity between the humans and pigs, the amino acid sequence of the human J chain (NCBI reference sequence NM_144646.3; version NM_144646.3; GI:189491638) was used as bait to identify the porcine J chain by homology-based search against the porcine EST (expression sequence tag) database. The porcine J chain homologous gene was identified from the cDNA library made from porcine alveolar macrophages (Genbank AK231006: version AK231006.1; GI:115546487). Using BLASTX, the J chain coding sequence was identified within this cDNA sequence, starting from the 72nd nucleotide (ATG) until the stop codon (TAA) at the 548th nucleotide.

The native signal peptide of J chain was identified using the prediction tool of Bendtsen et al. (2004), and this sequence was replaced by the signal peptide of 2S2 Arabidopsis seed storage protein. Thereafter, the codon usage in the entire coding sequence was optimized for expression in Arabidopsis seeds. The coding sequence for the endoplasmic reticulum retention signal (KDEL) was added to the 3' end (C-terminal end) followed by a stop codon, the DNA was chemically synthesized flanked by the attB1 and attB2 GATEWAY® cloning sites (Invitrogen) and the Kozak sequence (nucleotide-CCACC) was added upstream of the signal peptide during this process. The resulting DNA fragment was cloned into the multiple cloning site of pUC57 and recombined into the GATEWAY® pDONR221 plasmid, according to the instruction of the manufacturer. The resulting plasmid was indicated as pEJ.

Example 3: Cloning of the Porcine Secretory Component

The Secretory Component (SC) is a proteolytic cleavage product of the polymeric immunoglobulin receptor (pIgR). Structurally, the pIgR has five extracellular domains that are connected to a transmembrane-bound region by a linker peptide. Cleavage in the linker region results in the release of the five domains bearing polypeptide, which is then either found as free SC or associated with dimeric IgA (dIgA).

The sequence of the porcine SC was derived from the published sequence of porcine pIgR (Kumura et al., 2000; NCBI reference sequence: NM_214159; version NM_214159; GI:47523405). Given that the first five domains of the porcine pIgR are important for wrapping around the dIgA, the first 579aa length-spanning region until the 5th domain after the signal peptide (corresponds to the 585aa of human SC) was selected and defined as porcine SC. The endogenous signal peptide of pIgR was determined using the signal prediction tool (Bendtsen et al., 2004) and then in silico replaced by the signal peptide of the 2S2 seed storage protein of Arabidopsis seed. The nucleotide sequence of this porcine SC (1737 bp) was codon optimized for Arabidopsis seed expression and synthesized chemically with Kozak sequence upstream of the signal peptide, with flanking attB1 and attB2 sequences. The DNA fragment was cloned into the multiple cloning site of pUC57, and recombined into pDONR221 as described above, resulting in plasmid Pesc.

Figure 2:
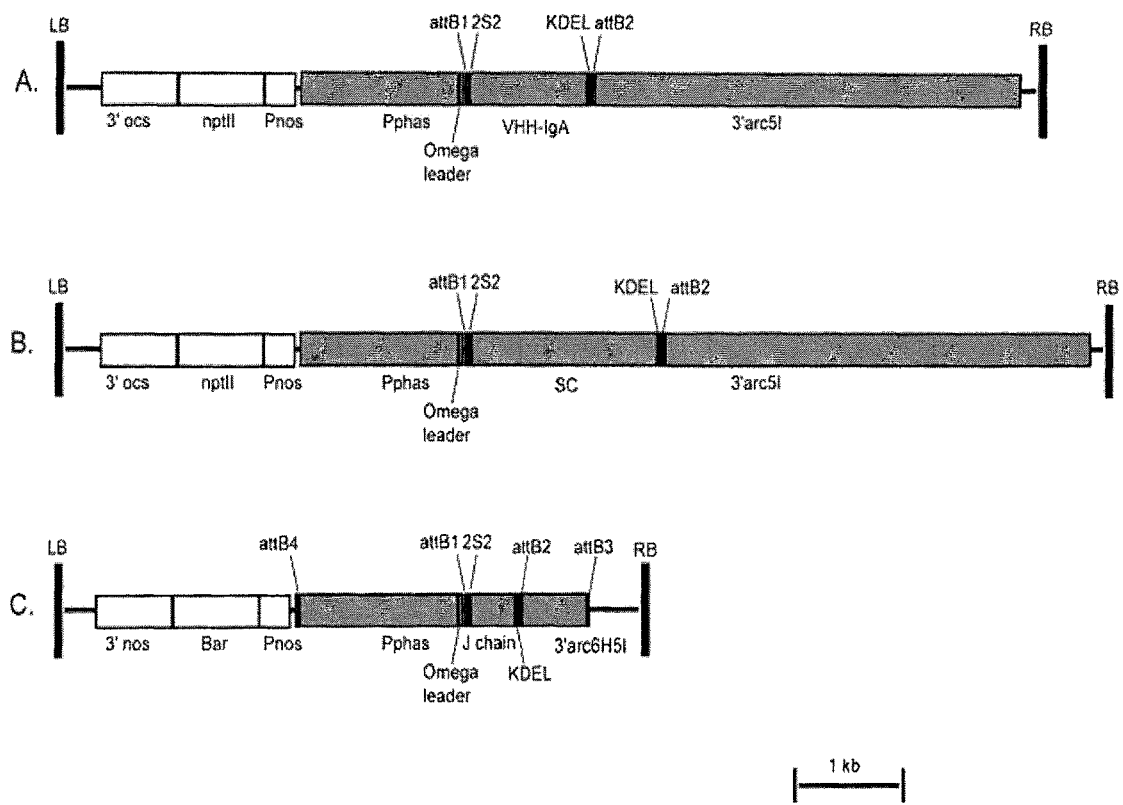
FIG. 2: Schematic representation of the T-DNA constructs for seed expression of anti-F4+ETEC secretory IgA antibodies. Abbreviations: LB, left border; RB, right border; VHH-IgA, fused coding sequence of the VHH-IgA; SC, porcine secretory component; J chain, coding sequence of the porcine J chain; Omega leader, 5' tobacco mosaic viral UTR; 2S2, signal peptide sequence of the 2S2 seed storage protein; KDEL, endoplasmic retention motif; attB1, attB2, attB3 and attB4, GATEWAY® recombination sequences (Invitrogen); Pphas, Phaseolin promoter; 3'arc5I, 3' arcelin terminator (4100 bp); 3'arc6H5I, 600 bp long 3' arcelin terminator sequence; nptII, neomycine phosphotransferase II gene; Pnos, nopaline synthase gene promoter; 3' ocs, octopine synthase terminator; Bar, phosphinothricin herbicide-resistant gene; 3' nos, nopaline synthase terminator.

Example 4: Cloning of the T-DNA Binary Vectors and their Transformation in Agrobacterium The pEVxA constructs (pEV1A, pEV2A, pEV3A, pEV4A), pEVxG constructs (pEV1G, pEV2G, pEV3G, pEV4G) and pESC were recombined by a GATEWAY® LR reaction into the destination vector pPhasGW (Morandini et al., 2011) according to the GATEWAY® instruction manual. The pPhasGW destination vector, the T-DNA region of which is shown in FIG. 2, contains an expression cassette with the GATEWAY® cloning site between the 5' regulatory sequences of the Phaseolin storage protein-encoding gene from Phaseolius vulgaris and the 3' regulatory sequences of the arcelin-encoding gene. The four expression clones with the VHH-IgA fusions are indicated as pXV1A, pXV2A, pXV3A and pXV4A; in a similar way, the VHH-IgG fusion T-DNA expression constructs are called pXV1G, pXV2G, pXV3G and pXV4G and the expression T-DNA vector carrying the SC-encoding gene was called pXSC.

To facilitate the identification of the co-transformed plants, the cassette for seed-specific expression of the J chain was cloned into the MultiSite GATEWAY® T-DNA vector pBm43GW,0 carrying a phosphinothricin (PPT) resistance-encoding gene as selection marker. Therefore, plasmids pEJ (carrying the J chain encoding sequence), pEPhas (bearing the Phaseolin promoter flanked by attL4 and attR1 sites) and pEArc600 (bearing the Arcelin terminator, flanked by attR2 and attL3 sites) were recombined into pBm43GW,0 and the resulting T-DNA expression plasmid was called pMXJ.

All junctions over the recombined sites were sequenced to confirm the exact recombination.

The T-DNA expression plasmids were transformed into the Agrobacterium strain C58 C1 Rif$^R$, carrying the vir plasmid pMP90, using electroporation (50 ng plasmid DNA for 40 μl competent cells using a 1 mm electroporation cuvette at 2.2 kV pulse). The transformant Agrobacterium colonies were selected on YEB plates with 20 μg/ml streptomycin and 100 μg/ml spectinomycin. The presence of the right plasmid was confirmed by restriction digest and sequencing. Single colonies with the correct plasmids were used to start cultures for glycerol stock and for *Agrobacterium*-mediated floral dip transformation.

Example 5: Production and Selection of Monomeric, Dimeric and Secretory VHH-IgA as Well as VHH-IgG Antibody-Expressing *Arabidopsis* Plants To produce plants expressing a complete IgA complex (with the VHH-IgA fusion, the J chain and the SC chain), three *Agrobacterium* strains carrying the plasmids pMXJ, pXSC and one of the plasmids pXV1A, pXV2A, pXV3A or pXV4A were inoculated in 10 ml YEB medium without any antibiotics overnight and when the $OD_{600}$ reached about 1.7, 3.3 ml of each of the three cultures were mixed together. This mixture was made up to 50 ml with dipping solution (10% sucrose and 0.05% SILWET® L-77 organosilicone surfactant (Fisher Scientific) solution in water) and used for the floral dip transformation.

For each of the four different VHH-IgA fusions (the four mixes: V1A+SC+J; V2A+SC+J; V3A+SC+J; V4A+SC+J), ten *Arabidopsis thaliana* (Col 0) plants were transformed by the floral dip method (Clough and Bent, 1998), to produce different formats of IgA antibodies bearing the four different antigen-binding domains.

Similarly, for single transformation in the case of VHH-IgG antibodies, the respective cultures were grown to the $OD_{600}$ of 1.7 in 10 ml of antibiotic-free YEB medium and then the cells were diluted to 50 ml volume with dipping solution. Five plants were dipped for each of the four VHH-IgG antibody constructs (single transformation).

The floral-dipped plants were allowed to grow until the ripe siliques become dry (about six weeks). The T1 seeds were then harvested.

Figure 3:
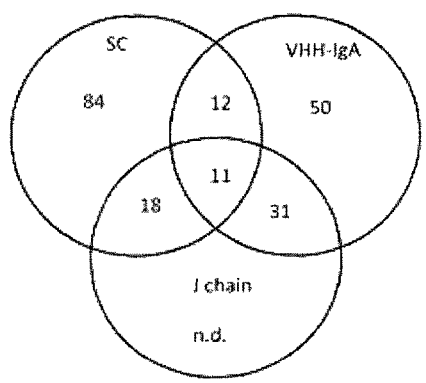
FIG. 3: Monomeric-IgA (mIgA), dimeric-IgA (dIgA) and secretory IgA-(sIgA-)expressing lines after triple co-transformation VHH-IgA, J chain and porcine secretory component. The table (Panel a) indicates the number of primary transformants identified from each of four VHH-IgA constructs, expressing VHH-IgA (mIgA); VHH-IgA and J chain (dIgA) or VHH-IgA, J chain and SC (sIgA). The transformation frequency is indicated in parenthesis. The Venn diagram (Panel b) shows the classification of the 206 primary transformants analyzed after co-transformation (n.d. stands for not determined).

From each floral dipped/transformed plant, approximately 1000 T1 seeds were first sown on 50 mg/L kanamycin-containing MS medium (Murashige and Skoog, 1962) [4.308 g/L Murashige and Skoog salts (Gibco BRL, Gaithersburg, Md.), with 0.5 g/L of MES (Duchefa), 10 g/L of sucrose, pH 5.7]. In this way, 206 primary transformants were selected for the triple co-transformed VHH-IgA plants (86 for V1A, 43 for V2A, 51 the V3A and 63 for V4A). A leaf piece from these 206 primary transformants was then placed on callus induction medium with PPT selection, to screen the transformants containing the J chain encoding gene. In parallel, the presence of the J T-DNA could be demonstrated by a diagnostic PCR in 60 different transformants (25 for VIA set, 6 for V2A, 16 for V3A and 13 for V4A set). Using a multiplex PCR set up with two primers (2PM-PCR) complementary to the regulatory elements on the T-DNA, the presence of either or both of the kanamycin resistance conferring VHH-IgA (VxA) T-DNA or SC T-DNA could be determined. From these results, all T1 plants were classified according to the three T-DNAs that they contained (Venn diagram, FIG. 3). The most interesting of these combinations were (i) the monomeric transformants (mIgA) with only VHH-IgA encoding T-DNA, (ii) the dimeric IgA transformants (dIgA) with IgA and J chain encoding T-DNA and (iii) the sIgA transformants with all three T-DNAs carrying the VHH-IgA, J chain and SC coding sequences (Venn diagram, FIG. 3).

For the plants dipped for production of VHH-IgG antibodies (single transformation), approximately 1000 seeds per floral dipped plant were sown on 50 mg/L kanamycin-containing MS medium and 24 primary transformants were isolated for each of the four VHH-IgG antibodies (V1G, V2G, V3G and V4G).

To assess the accumulation of the assembled, functional VHH-IgA antibodies classified as mIgA, dIgA and sIgA in the seeds of the transformed *Arabidopsis* plants and the VHH-IgG, an ELISA-based assay with immobilized FaeGac antigen was used. To start, 5 mg T2 seeds harvested from each individual T1 transformant were placed in individual microtubes, a steel ball of 4 mm was added and the tubes were closed and snap chilled in liquid nitrogen. The frozen seeds were crushed in a mill (Mixer mill MM400-Retsch) for 20 seconds at 20 hertz. Then, 600 µl cold extraction buffer (50 mM Tris-HCl pH 8.0, 200 mM NaCl, 5 mM EDTA, 0.1% TWEEN®20 (polysorbant-type nonionic surfactant, Sigma-Aldrich)) was added to the crushed seeds and the mixture was vortexed to resuspend all the seed powder and dissolve the soluble fraction. The tubes were centrifuged for 10 minutes at 3000 g so that the oil/lipid phase was separated from the aqueous phase, and 300 µl protein extract (middle clear aqueous phase) was taken for analysis.

The characterization and quantification of the seed produced VHH-Fc antibodies via sodium dodecyl sulfate-polyacrylamide gel electrophoresis (SDS-PAGE) as well as immunoblotting, was done as previously described (De Buck et al., 2011). The relative quantification of the FaeG binding functional antibodies in the seed extract was determined via ELISA as described below.

Figure 4:
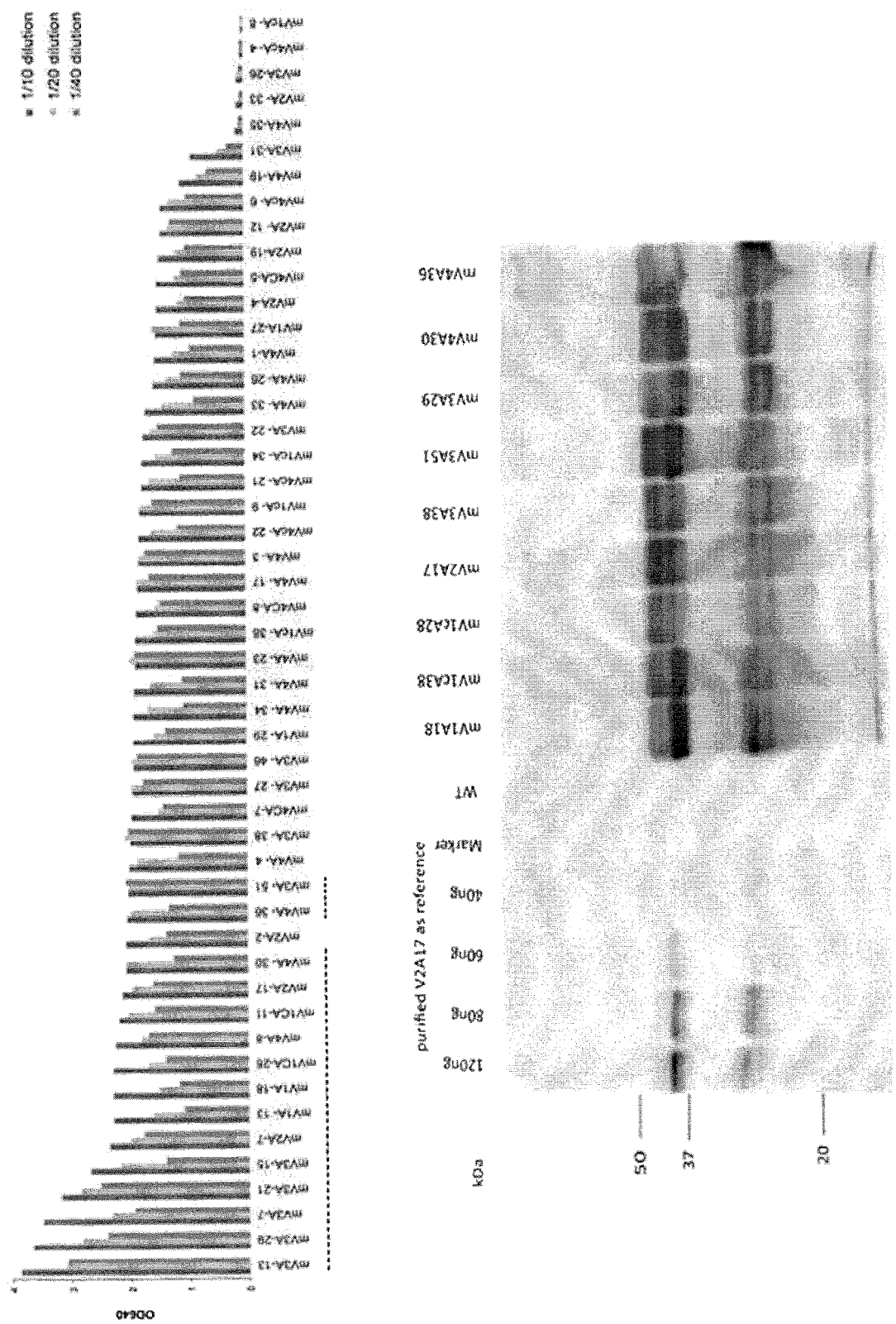
FIG. 4: Selection and characterization of monomeric IgA-producing plant lines. The accumulation of functional mIgA as determined by ELISA (Enzyme-Linked Immunosorbant Assay) in the 50 lines was comparable for most of the lines. Under reducing conditions, the VHH-IgA in nine high-expressing single locus mIgA lines shows occurrence of four bands at the expected molecular weight of 37 kDa and excessive proteolitically cleaved lower molecular weight bands around 25 to 20 kDa (bottom gel picture).

Identification of Transformants Expressing High Amounts of Functional VHH-Fc Antibodies Multisorb ELISA plates (Nunc 439454) were coated overnight with 1 µg/ml concentration of purified recombinant FaeGac in $NaHCO_3$ buffer pH 8.2, in a volume of 100 µl per well at 4° C. The next morning, the coating solution was decanted and the wells were washed by flushing and decanting the plate five times with 300 µl of 0.1% TWEEN®20 in PBS. Residual droplets were removed by knocking the plate on absorbent paper. The wells were blocked with 150 µl of 2% skimmed milk in PBS and incubating the plates at room temperature (25° C.) for 90 minutes. Plates were then washed again and 100 µl serial dilutions of plant extracts (typically 1/100, 1/200, 1/400, 1/800) made in 2% skimmed milk in PBS were added to the wells and incubated for 90 minutes at room temperature. After incubation, the wells were washed again as described above. For detection of bound, seed-produced VHH-Fc fusion-based antibody, specific anti-Fc antibody was chosen. For monomeric VHH-IgA antibodies, 100 µl of the polyclonal anti-porcine IgA antibody conjugated to horseradish peroxidase HRP (AbD serotech AA140P), in a dilution of 1/10,000 in 2% skimmed milk, was used. While detecting the plant-produced VHH-IgG antibodies, 100 µl of polyclonal anti-porcine IgG produced in rabbit (Sigma A5670) conjugated to HRP diluted 1/40,000 in 2% skimmed milk was used. After addition of the primary conjugated antibody, the plate was incubated for 90 minutes at room temperature and washed. Then, 100 µl ready-to-use HRP substrate TMB (3,3',5,5' tetramethylbenzidine; Sigma) was added per well, and the plates were kept in the dark for 30 minutes. The intensity of the color was measured at 640 nm (VERSAMAX™ Molecular Devices, Sunnyvale, Calif.). The overall accumulation of functional VHH-IgA was reasonably similar for all four VHH-IgAs (FIG. 4). Amongst the pool of 50 monomeric VHH-IgA-expressing lines, 15 high expressing lines (indicated with dotted line in FIG. 4) were selected for further characterization and up-scaling. Of these 15 lines, five were expressing mV1A, two expressing V2A, four expressing mV3A and four expressing mV4A. From these 15 lines, nine transformants were retained because they had single locus T-DNA insertion as determined by a 3 to 1 segregation ratio of T2 plants on kanamycin-containing medium and a germination frequency of more than 40% of the seeds.

Within the 24 transformants screened for each VHH-IgG antibody, the range for variation for the V2G was the highest (maximum expression about 15% of TSP) followed by V1G (maximum expression about 10% of TSP), while V3G and V4G antibodies (maximum expression about 2% of TSP) had a relatively low range of variation in accumulation of functional antibody. From the ELISA readouts, the relative accumulation of functional antibodies in the respective transformants could be classified as high, medium and low expressers. High-expressing VHH-IgG transformants with single locus insertion were identified and homozygous lines were established for bulk scale up.

Figure 5:
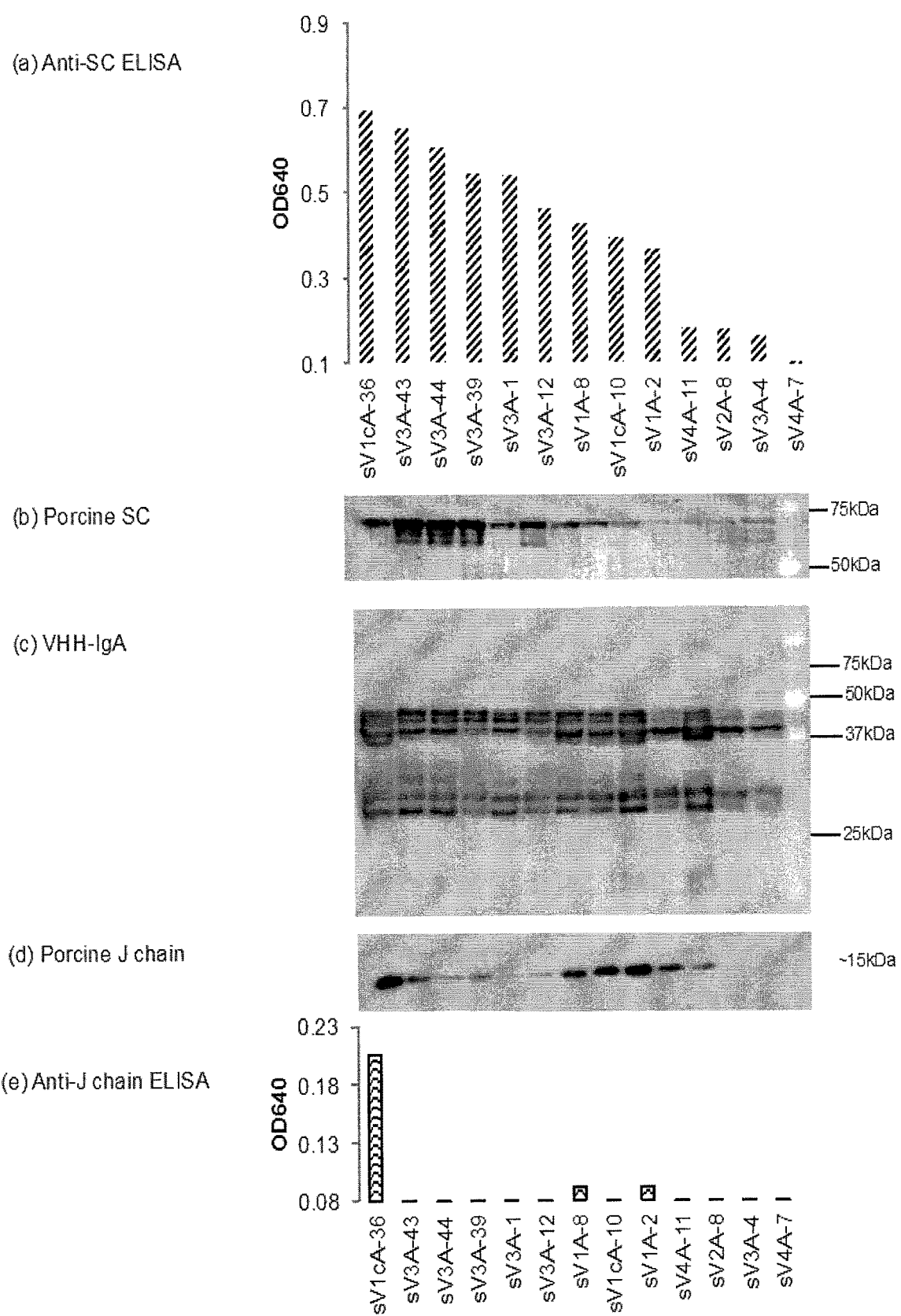
FIG. 5: Characterization sIgA produced in *Arabidopsis* seeds.

Identification of Lines Expressing High Levels of Assembled Dimeric and Secretory VHH-IgA-Based Antibodies In order to determine the transformants with high accumulation of functional dimeric IgA [4×(VHH-IgA)+J chain] and sIgA antibodies via ELISA, all the steps until seed extract addition into FaeGac-immobilized wells were followed as described above. To detect dimeric IgA antibody, the anti-J chain monoclonal antibody (Thermo Scientific MA1-80527) was used, diluted 1/1000 in 2% skimmed milk in PBS. Whereas, to detect the secretory IgA antibody [4×(VHH-IgA)+J chain+secretory component], the monoclonal anti-pig secretory component antibody (Thermo Scientific MA1-80544) was used. The primary antibody was incubated for 90 minutes followed by five washes (0.1% TWEEN®20 in PBS). The secondary antibody, anti-mouse polyclonal made in sheep conjugated to HRP (Amersham Bioscience, NA931V) was used, diluted 1/5000 in 2% skimmed milk in PBS, the plate was incubated at room temperature for 1 hour. Thereafter, the plate was washed and developed as above-mentioned ELISA, where 100 µl of the substrate TMB was added into each well. After incubation for 30 minutes, a blue color developed, which was read at 640 nm, using the VERSAMAX™ tunable microplate reader (Molecular Devices, USA). Similarly, as in the case of mIgA (and VHH-IgG), from the optical density measured at 640 nm, the plants were ranked according to the expression levels of functional dimeric (FIG. 6) or secretory IgA (FIG. 5).

sSIgA

For the sIgA-expressing plant, only nine of the 15 had a signal higher than the negative control (OD640 of wild-type; negative control was 0.04). Only fully assembled functional sIgA were detected in this ELISA as plants expressing just the VHH-IgA+J chain (dIgA), or the ones expressing SC and J chain did not give signal above the background (FIG. 5). Further, ELISA-based analysis with anti-J chain antibody within these nine sIgA-expressing lines reviled the occurrence of bi-species, i.e., dIgA alongside sSIgA in three plants. Of these three, sV1cA36 had a much higher titer as compared to sV1A8 and sV1A2 (FIG. 5, section (e)). The SDS-PAGE immunoblot analysis on these nine sIgA-producing lines confirmed the accumulation of J chain in all of these sIgA-producing seeds (FIG. 5, section (d)). This suggests that the presence of the SC in sIgA masks the interaction of the monoclonal anti-J chain. In the three lines, the high ratio of expression of J chain to SC resulting in the formation of J chain-bearing dimeric IgA (especially in the line sV1cA36) alongside the sIgA antibodies. The relative accumulation level of each of the elements of sIgA under reducing conditions was further investigated by immunoblot analysis. The results showed that the expression of the SC in the nine sIgA lines correlates with the relative expression of assembled sIgA as determined by ELISA (FIG. 5, sections (a) and (b)).

dIgA

Figure 6:
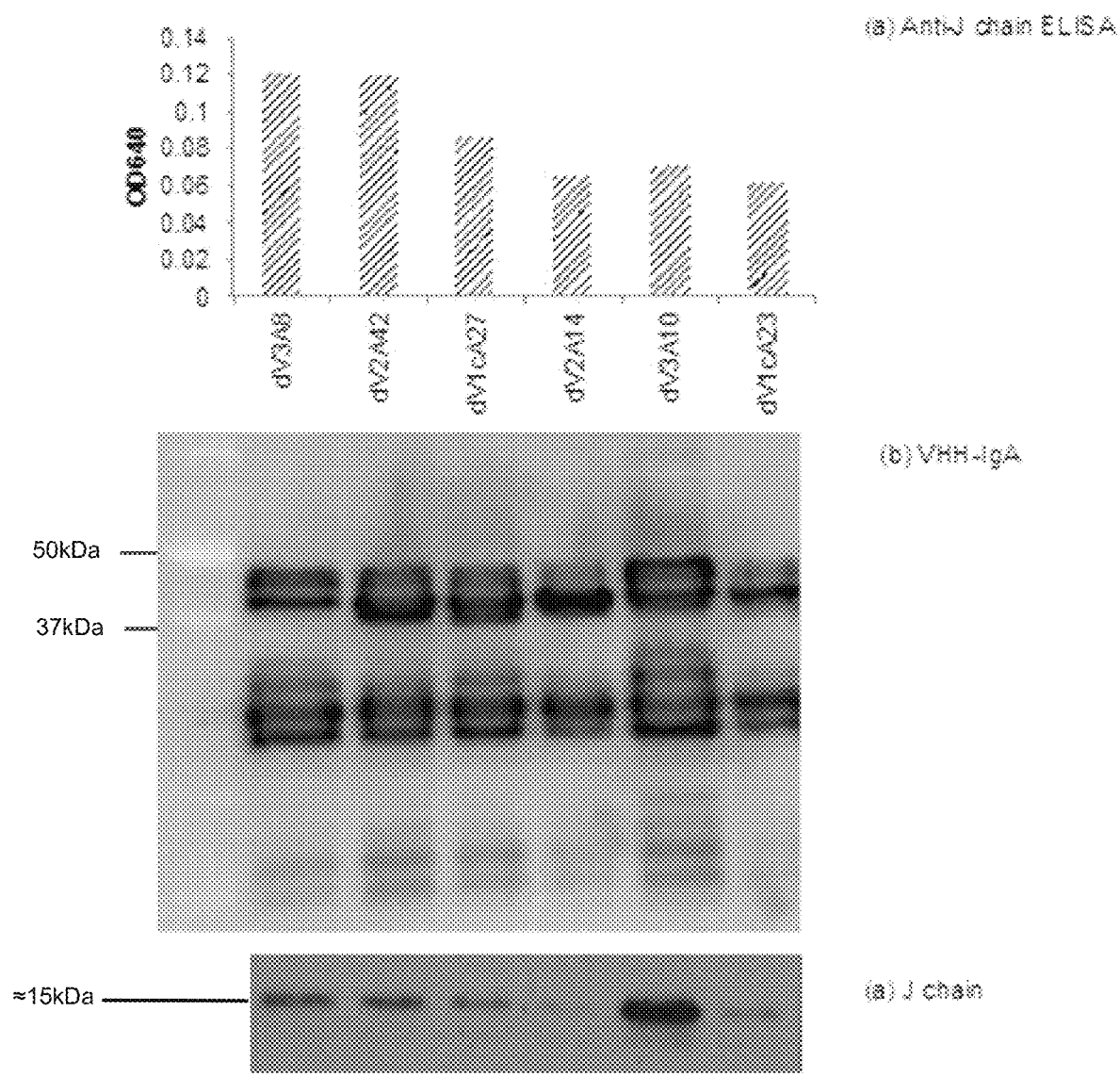
FIG. 6: Characterization the dIgA-producing seeds for assembled functional antibodies.

Within the transformants-bearing J chain and VHH-IgA T-DNA, the ELISA using anti-J chain monoclonal antibody (Thermo Scientific MA1-80527) (as described above) showed seven plant lines exclusively expressing assembled functional dimeric IgA. The results indicate that the J chain specifically interacts with the VHH-IgA and does not bind to the antigen FaeG in the absence of VHH-IgA. Among these seven dIgA-producing lines, the plant line producing dV4A2 did not produce enough seed for further analysis and propagation, and the remaining six lines were characterized under reducing conditions by immunoblot. The immunoblots developed with anti-SC, anti-porcine IgA and anti-J chain antibody confirmed that these seven lines did not express SC, and that the dimeric IgA is composed entirely of VHH-IgA chains and the J chain (FIG. 6). The VHH-IgA accumulation in all six lines was similar (FIG. 6, section (b)). Whereas the accumulation of the functional complex (ELISA) correlated with the expression of the J chain in five out of the six lines (FIG. 6, sections (a) and (c)), the line dV3A10 showed the highest amount of J chain (FIG. 6, section (c)), but had lower signal for functional dIgA in ELISA (FIG. 6).

The VHH-IgA expression in the selected sSIgA, dIgA, and mIgA transformants, was analyzed further by immunoblot under reduced conditions, with purified standards as reference (FIGS. 9A-9E).

Surprisingly, under reduced conditions on SDS-PAGE analysis, instead of the expected single 39 kDa VHH-IgA band, four heterologous bands were observed ranging from 37 kDa until 50 kDa, and additionally, lower molecular weight bands of approximately 20 kDa and 27 kDa were seen. These lower molecular weight bands could result from proteolysis in the seed. The bands were not seen in the wild-type control seed extract and were specific for porcine IgA Fc fusions as they were not seen with IgG Fc fusions. Glycosylation in the VHH-IgA could explain the quadruplet bands.

Results obtained from FaeG (antigen) binding immunoprecipitation assay followed by immunoblot, suggested that all four VHH-IgA bands within the expected molecular weight of 37 kDa to 50 kDa recognized the antigen. Measuring the sum of the intensity of the four VHH-IgA bands from immunoblot, using affinity-purified seed made antibody or purified porcine IgA from swine serum as reference standards reviled that VHH-IgA accumulated up to 0.58±0.09% of seed weight, i.e., approximately 2.5% of the total soluble protein (TSP) in the segregating T2 seeds. The accumulation of antibodies in the homozygous T3 seed stocks from the corresponding single locus mIgA lines was about 0.64±0.11% of seed weight.

The accumulation of the VHH-IgA in the sIgA and the di-IgA lines was also similar to the expression seen in the monomeric VHH-IgA lines, with an average of 0.5% accumulation in T2 seeds and an increase in some T3 homozygous seed stock to an average of 0.7% or 0.8% of seed weight. With a few purified mIgA standards, further evaluation via ELISA showed that only half of the measured sum of the four VHH-IgA bands is functional in solution. From calculations based on ELISA and immunoblot data, it was estimated that the overall functional IgA in the oligomeric pool (SIgA, dIgA and mIgA) is about 1% of the total soluble protein, which is 0.2% of the seed weight.

Example 6: Glycosylation and Proteolytic Degradation of VHH-IgA as Factors Affecting Assembly of IgA To determine the nature of N-linked glycans present on the recombinant protein, the N-link glycosidase Endo H and or PNGase F were used according to the manufacturer's instructions. The protein was denatured by heating at 100° C. for 10 minutes in a denaturing buffer containing 5% SDS and 0.4 M DTT. Then the enzyme was added and incubated at 37° C. for 60 minutes. The reaction was stopped by adding Laemmli buffer and heating the sample at 98° C. for 8 minutes. This sample was loaded onto an SDS-PAGE gel and immunoblotted, using anti-pig IgA polyclonal antibodies to determine the shift in the mobility of the protein after removal of N-linked glycans.

Figure 7:
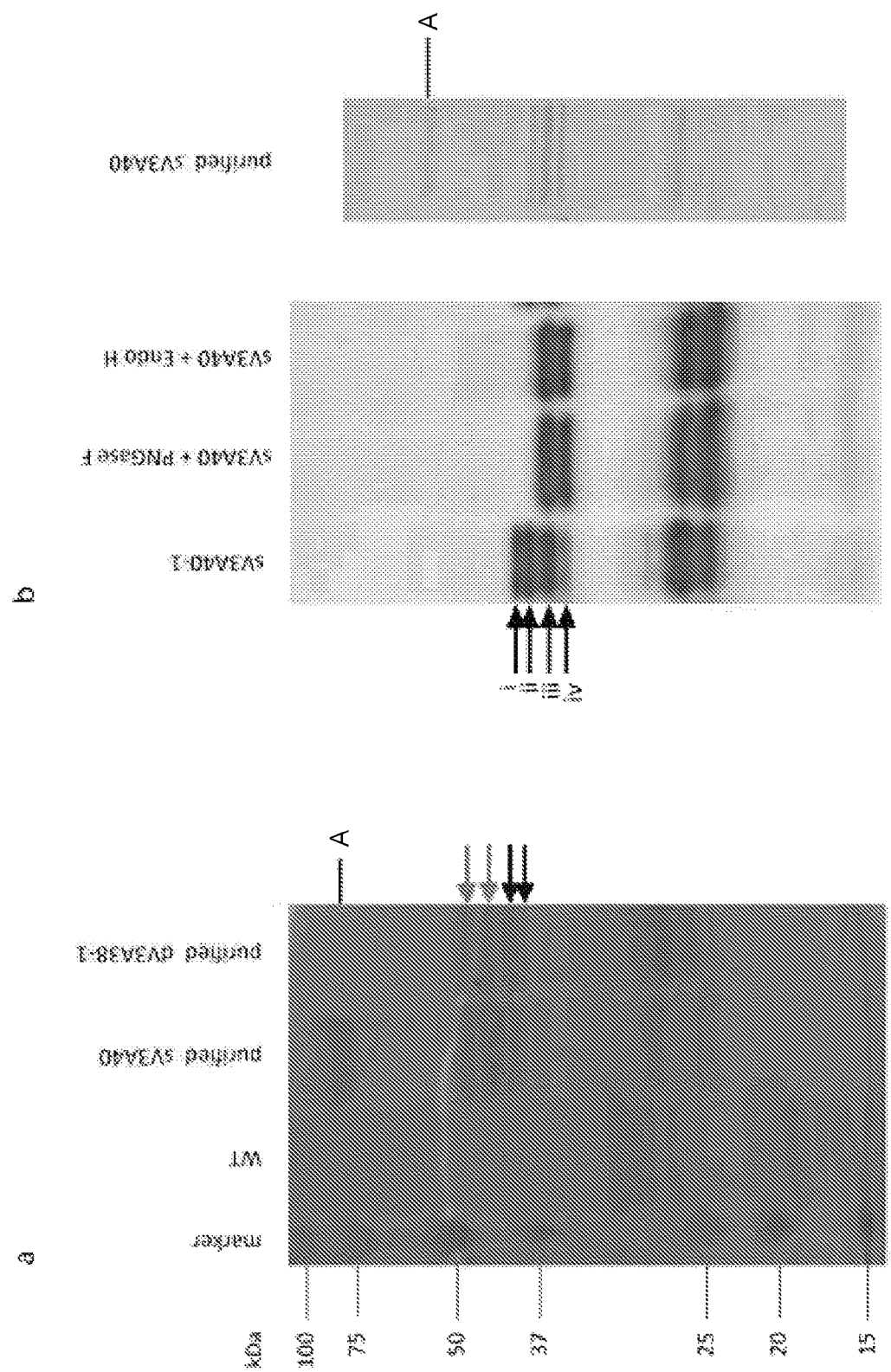
FIG. 7: Glycosylation analysis IgAs produced in seed. (Panel a) the four VHH-IgA bands: the upper two bands were stained pink indicating the presence of glycans (staining with periodic acid; upper two arrows), while the lower two bands (counterstained with Coomassie) were un-glycosylated (black arrows). The bar (A) indicates the porcine secretory component (~75 KDA), which is also glycosylated. (Panel b) The staining results were confirmed by endo glycosidase analysis with PNGase F and EndoH reducing the four bands (black arrows labeled i, ii, iii, iv) to two bands. The bar (A) vivo experimentalindicates the porcine secretory component (~75 KDa), which is also glycosylated.

The VHH-IgAs expressed in the *Arabidopsis* seeds showed the presence of the four bands under reducing conditions. The relative abundance of each of the four bands differed from plant to plant, but the bands were present in all the lines irrespective of the co-expression of the SC and/or the J chain. The IgA heavy chain is heavily glycosylated and bears both N-linked and O-linked glycans in its natural system, as well as when recombinantly expressed in mammalian and plant systems (Karnoup et al., 2005). Glycoprotein staining of these four bands with Periodic acid-Schiff's reagent (Kapitany and Zebrowski, 1973), showed that only two of the VHH-IgA bands were glycosylated (FIG. 7); the lower two bands (counter-stained with Coomassie) did not seem to bear any glycan. Upon endoglycosidase digest with PNGase F and EndoH (which excises the N-linked glycans by specifically cleaving at the beginning of the first GlcNAc or between the first and second GlcNAc, respectively), the high molecular weight bands were reduced to the molecular weight of the two lower bands (FIG. 7), thus confirming that only the two high molecular weight proteins are glycosylated. The two lower molecular weight bands have a different molecular weight due to truncation of the terminal peptide by proteases. The glycosidase analysis of a V2A and V3A lines suggests that there are differences in glycosylation for the different VHHs fused to the porcine IgA.

Along with glycosylation, the proteolytic cleavage also determines the accumulation, assembly and functionality of the antibody. In the plant extract, a substantial amount of proteolytically cleaved VHH-IgA fragments was observed. The total amount of the degraded protein was almost equal to the level of accumulation of the four intact VHH-IgA bands in total.

Example 7: Expression of V2G, V3G, and V2A in the Seeds of Pea and Soybean

Transformation in Pea (*Pisum sativum*, Cv Greenfeast)

The plasmid DNA of the expression vectors pXV2G, pXV3G and pXV2A was transformed into the *A. tumefaciens* strain EHA105 (Hood et al., 1993) by electroporation. Transformed colonies are selected on YEB-agar plates with spectinomycin (100 µg/ml) and streptomycin (20 µg/ml) selection, the presence of expression plasmid in these colonies was reconfirmed by PCR. Subsequently, single colonies were streaked out to start bulk liquid culture and an aliquot of the culture was preserved in glycerol. Using this *Agrobacterium* strain bearing one of the three expression plasmids, the pea embryo explants are transformed in accordance with the protocol described by Mikschofsky et al., 2009, and Polowick et al., 2000.

Transformation in Soybean

To allow phosphinothricin herbicide-based selection for the transformed soybean plant, the entry clones pEV2G, pEV3G, and pEV2A were recombined into MultiSite GATEWAY® cassette pBm43GW,0 (Karimi et al., 2005), together with the entry clones pEPhas (bearing the β-phaseolin promoter) and pEArc600 (bearing the 600 bp long arceline terminator bearing 3' regulatory sequence), according to MultiSite GATEWAY® Instruction Manual (Invitrogen). The three resultant expression vectors for production of antibody V2G, V3G and V2A were named pMXV2G, pMXV3G, and pMXV2A, respectively. These three expression plasmids were introduced into *A. tumefaciens* strain EHA101 (Hood et al., 1986) and used for transformation of soybean (*Glycine max* cv William 82). The soybean transformation was subcontracted to the Plant Transformation Facility of Iowa State University and was performed in accordance with U.S. Pat. No. 7,473,822 (Paz et al., 2004).

Example 8: In Vitro Inhibition of the Pathogenic F4+ETEC to Gut Villous Enterocytes For the purification of the antibodies produced in *Arabidopsis* seed, commercially available affinity-based resins were used. For purification of the VHH-IgG constructs, Protein A Sepharose columns (HITRAP® rProtein A FF, GE Healthcare) were used in an AKTA™ liquid chromatography system. All the chromatographic steps were performed at 4° C. The column was equilibrated with about 10 column volumes with binding buffer (50 mM Tris-HCl pH 8.0, 200 mM NaCl, 5 mM EDTA, 0.1% TWEEN®20). The seed extract made in the protein extraction buffer (pH 8) was filtered through 0.45 µm filter and loaded onto the column at a flow rate of 1 ml/minute without exceeding a pressure of 0.2 Mpa. After passing the protein solution, the column was equilibrated again with 10 column volumes of binding buffer and then washed twice: first with 100 mM Tris-HCl pH 8 followed by a wash with 10 mM of Tris-HCl pH 8 (10 column volumes each). The antibodies, bound on the column were then eluted using 0.1 M of glycine at pH 3. Fractions of 450 µl were collected into microcentrifuge tubes pre-dispensed with 50 µl of 1 M Tris pH 8 to neutralize the acidic pH of the eluted fraction. Fractions comprising the purified antibodies were identified by measuring the $OD_{280}$; these fractions were then pooled.

For purification of VHH-IgA antibodies, an SSL7/Agarose resin (InvivoGen) was used, either on 5 cm long columns plugged into an AKTA system or by a batch system, depending upon the quantity of purified antibodies desired. The resin was washed and equilibrated with the binding buffer. The protein extract was applied to it and the unbound proteins were washed away with PBS. The bound antibodies were eluted by changing the pH with 0.1 M glycine pH 3. The eluted fraction was neutralized with 1 M Tris pH 7.2.

To determine whether the in planta made antibodies inhibit the F4+ETEC bacterial binding to the gut, an in vitro test was performed in accordance with the protocol described by Coddens et al. (2009). In summary, the intestinal gut villi were obtained from a euthanized pig, fixed (160 mM Krebs-Henseliet buffer, pH 7.4 containing 1% (v/v) formaldehyde for 30 minutes at 4° C.) and a sample was then tested for the presence of the receptor by incubation with F4+ETEC strain, such receptor-positive villous enterocytes were then preserved in Krebs-Henseliet buffer at 4° C. for further use.

The wild-type F4+ETEC strain GIS26 (serotype O149: k91:F4ac, LT+, ST+, STb+) (Cox and Houvenaghel, 1993) was cultured on brain heart infusion agar plates (Oxoid, Basingstoke, Hampshire, England) at 37° C. for 18 hours, then the cells were collected from the plate by gently flushing with 1% (w/v) D-mannose in PBS (PBSM) (approximately 3-4 ml). The mannose prevents adhesion mediated by type 1 pili. The optical density (OD) of the cells was measured at a wavelength of 600 nm. An OD of 1 corresponds to $10^9$ bacteria per ml. GIS26 bacterial cells ($4 \times 10^8$) were incubated with either seed extract bearing anti-ETEC antibodies or purified anti-ETEC antibodies, in a final volume of 450 µl made up by PBSM. The antibodies were incubated for one hour on a rotation wheel. After 1 hour, the villi were washed with Kreb-Henseliet buffer, and 50 µl of these villi were added to the bacteria and seed extract mixture, then incubated again for 1 hour on the rotating wheel. After the incubation, the villi-antibody mixture (~20 µl) was taken and analyzed by phase contrast microscopy at a magnification of 600 times. All the samples were blinded to eliminate experimental bias while counting the number of bacteria bound to the villi surface. A villi section of about 50 µm in length was selected and the number of bacterial cells attached was counted. For one sample, 20 randomly chosen sections were counted. The results were expressed as an average number of bacteria attached to 250-micrometer length of the villi surface.

Figure 8:
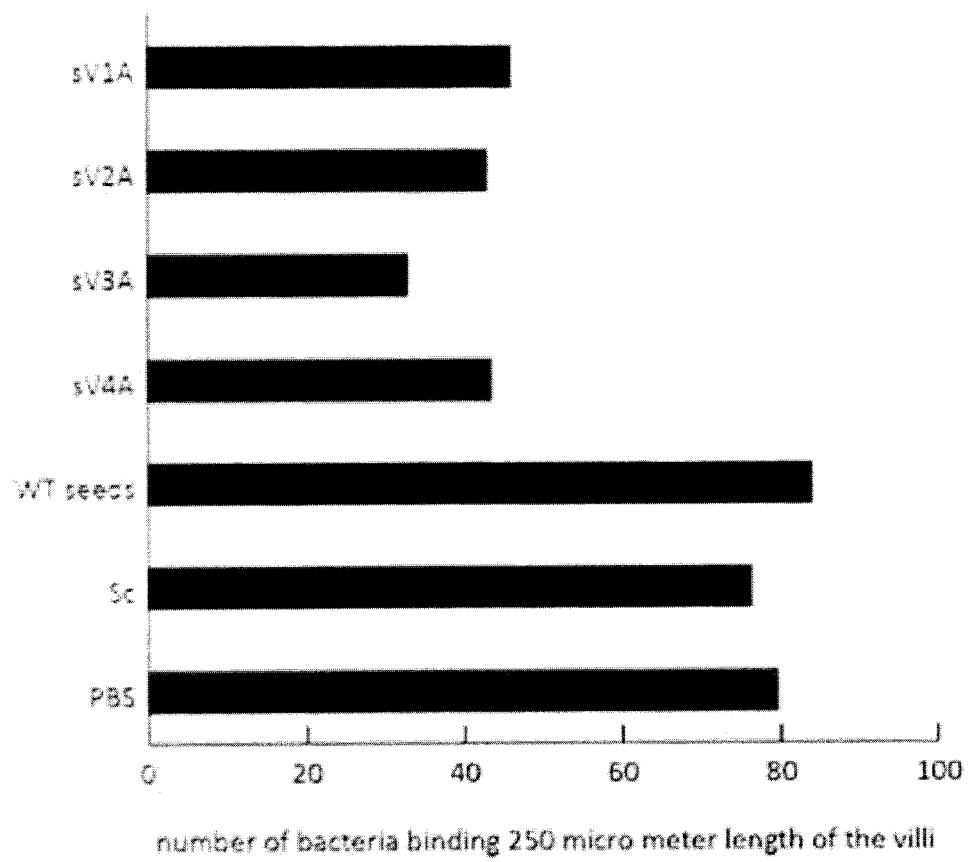
FIG. 8: Inhibition of the bacterial attachment to the porcine gut villous enterocytes in vitro. All four sIgA prevent attachment of the F4+ETEC bacterial cells to microvilli. Secretory Component (SC) alone does not inhibit the F4+ETEC attachment, nor does wild-type (WT) seed extract, both of which show attachment of bacteria similar to phosphate buffer saline (PBS) used as negative control.
Figure 9B:
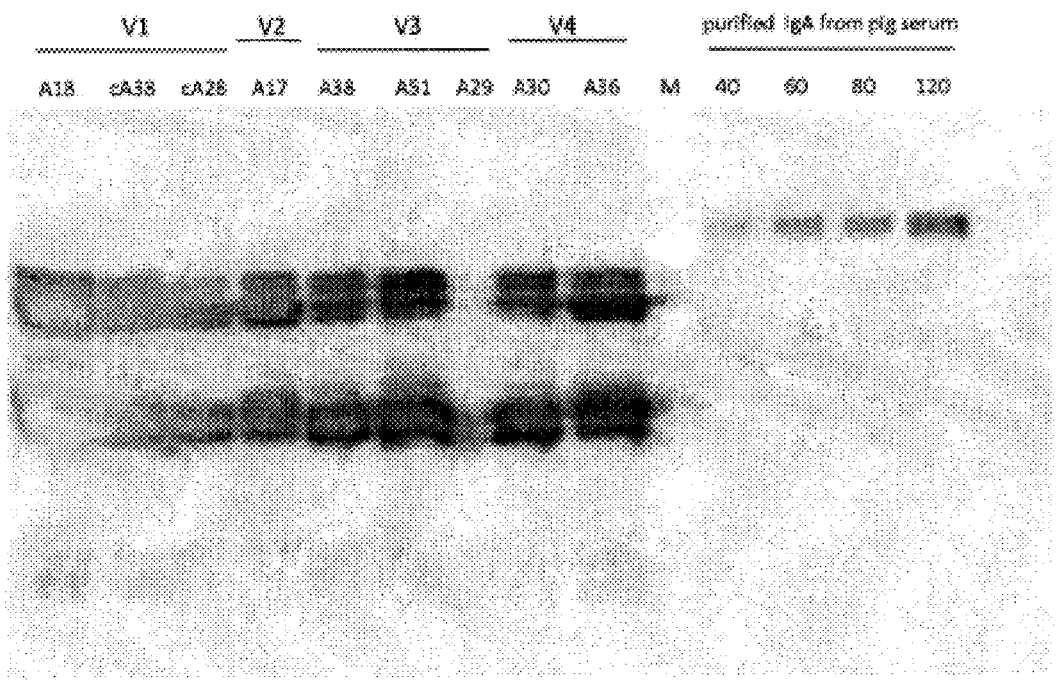
Figure 9C:
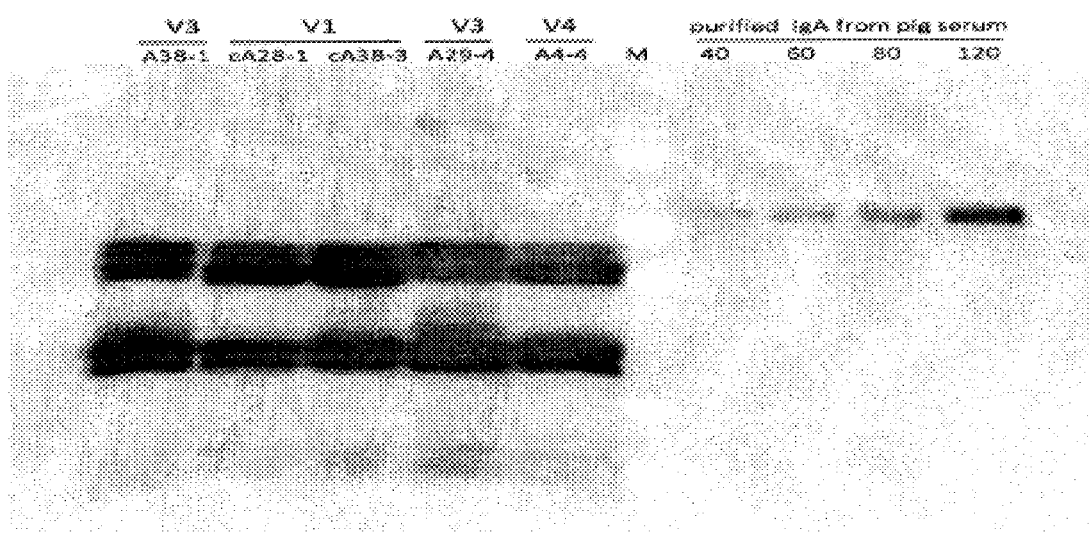
Figure 9D:
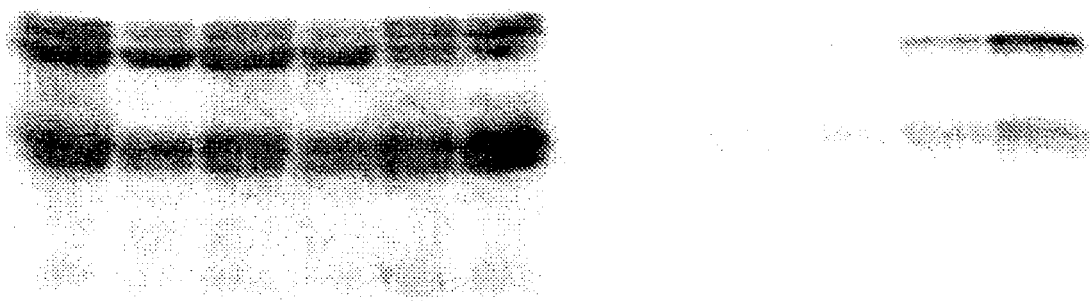
Figure 9E:
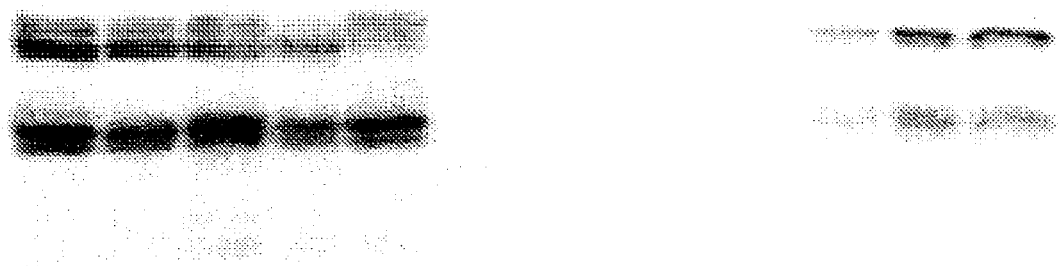

All the IgA antibody formats (four VHH×three IgA formats) were effective in inhibiting the bacterial attachment (FIG. 8). This semi-quantitative assay does not allow the quantitative comparison of efficacy between the mIgA, dIgA and sIgA. The SC alone could not inhibit the bacterial attachment nor did the wild-type *Arabidopsis* (Col 0) seed extract (FIG. 8).

Example 9: Palatability of *Arabidopsis* Seeds in Piglet Diet

Before the in vivo feed trial, it was necessary to evaluate the palatability of *Arabidopsis* seeds in the feed of young piglets. Eight piglets were weaned and housed in individual feeding cages for two weeks. Each piglet received 1 kilogram of feed per day that could be consumed ad libitum over the whole day. Leftover feed from the previous day was collected and weighed to determine the daily feed consumption. For the first week, all eight piglets were given identical creep feed to acclimatize all the piglets to solid feed. Once acclimatized, the feed for four piglets was replaced with piglet starter feed (ILVO) for the control group while four other pigs received the same starter feed supplemented with 2% milled *Arabidopsis* wild-type (Col 0) seeds. The consumption pattern of all the piglets was compared at the end of two weeks and the influence of adding 2% *Arabidopsis* seeds on the consumption of feed was evaluated.

The control group on an average consumed about 522±47 grams of feed per day, while piglets receiving 2% *Arabidopsis*-containing feed on an average consumed 593±99 grams of feed per day. The results obtained showed that the piglets accepted the *Arabidopsis*-containing feed. The FCR was within 1.3, which is an average standard FCR reported for different feeds for piglets at this age.

TABLE 1

*Arabidopsis* seed (wild-type seeds) flour at 2% inclusion rate in piglet feed was palatable

| | Daily average feed intake (in grams) | | | | | | Total weight gain in 6 days (in kg) | Feed to weight conversion ratio (FCR) |
|---|---|---|---|---|---|---|---|---|
| | Day 1 | Day 2 | Day 3 | Day 4 | Day 5 | Day 6 | | |
| Starter feed without wild type *Arabidospsis* seeds | 380 ± 40 | 405 ± 40 | 475 ± 70 | 530 ± 80 | 640 ± 100 | 0.700 ± 40 | 2.850 ± 0.29 | 1.10 ± 0.04 |
| Starter feed with wild type *Arabidospsis* seeds | 445 ± 40 | 510 ± 70 | 545 ± 100 | 645 ± 140 | 690 ± 140 | 0.725 ± 150 | 2.925 ± 0.57 | 1.23 ± 0.16 |

Example 10: Feed-Challenge Experiment: Evaluation of Protection Conferred by Seed Made Anti-F4+ETEC Antibodies on Experimental Challenge Selection of Piglets:

Suckling piglets were screened for anti-F4+ETEC seronegative status, and such seronegative pigs were further evaluated for their susceptibility by genotyping mucine receptor by RFLP, is detailed as below.

Blood Sampling and Serum Processing

About 5 ml blood was withdrawn from the jugular vein of the piglets from a conventional Belgian porcine farm at 3 days of age and a part of this was aliquoted in microcentrifuge tubes pre-dispensed with 10% EDTA as an anti-coagulant. The remaining blood was allowed to clump by maintaining at 37° C. for 1 hour, and the serum fraction was taken. This serum fraction was centrifuged at ~20,800 g for 10 minutes at 18° C. to pellet any blood clumps, and obtain a clear serum fraction. This supernatant was then heat inactivated for 56° C. for 30 minutes and then defatted by kaoline treatment. For the latter, one part serum was added to four parts of kaoline solution, vortexed well, maintained at room temperature for 30 minutes, and centrifuged for 10 minutes at 14,000 rpm at 18° C. The clear defatted serum fraction was stored at −20° C.

Screening Seronegative Piglets by F4-Specific ELISA

Piglets were screened for their F4+ETEC serostatus using a dedicated ELISA assay. The maxisorb ELISA multititer plates were coated for 2 hours at 37° C. with 100 µl of anti-F4 monoclonal antibody dissolved in PBS at a concentration of 1 µg/ml. After 2 hours, the plates were decanted, tapped on absorbent paper, and 300 µl of 0.2% TWEEN®80 (nonionic surfactant and emulsifier, Sigma-Aldrich) was added as blocking agent. The plates were incubated at 4° C. overnight. Subsequently, the plates were washed four times with 0.2% TWEEN®20 in PBS. One hundred microliters of purified F4 fimbriae diluted in dilution buffer (3% bovine serum albumin in PBS) at a concentration of 25 µg/ml was added and the plate was incubated for 1 hour at 37° C. After incubating, the plates were washed as before. Serum samples diluted 4× in dilution buffer were added in duplicate. At the same time, seronegative and seropositive reference serum was added as negative and positive control, respectively. After another hour of incubation at 37° C., the plates were washed, and 100 µl of anti-porcine goat polyclonal antibody conjugated to HRP diluted 1:5000 in dilution buffer was added to each well. The plate was maintained at 37° C. for one hour. Finally, 50 µl of substrate ABTS (2,2'-Azinobis[3-ethylbenzothiazoline-6-sulfonic acid]-diammonium salt; 1 mg/ml) (Roche) was added and OD was measured at 405 nm wavelength every 5 minutes, over a period of 30 minutes.

The OD of the piglet serum samples was compared to the controls and the seronegative piglets were selected.

Genotyping of Seronegative Piglets Expressing F4+ETEC Receptor

Seronegative piglets were screened for presence of F4ac receptor by the non-invasive mucin 4 polymorphism-based PCR-RFLP assay as described by Rasschaert et al. (2007) based on the patent WO2004/048606-A2. The genomic DNA was extracted from the blood cells from the uncoagulated blood fraction using 10% EDTA as anti-coagulant. The nucleated blood cells were pelleted by centrifugation for 1 minute at 3800 g, the supernatant was discarded and the cells were washed two times with PBS. To the washed cells, 200 µl of proteinase K buffer (50 mM KCL, 20 mM Tris-HCL, 2.5 mM, $MgCl_2$ 2.5% TWEEN®20, pH 8.3) with 10 µg proteinase K (Gibco) was added, and incubated at 37° C. for 1 hour. The enzyme was then deactivated by incubation at 95° C. for 10 minutes. Five microliters of this crude mixture containing the genomic DNA was used in a 20 µl volume PCR; containing 1× Taq buffer, 1 unit of Taq polymerase, 2 mM $MgCl_2$, 200 µm of each dNTPs and 1 µM of each of the forward and reverse primers (5' GTGCCTTGGGTGAGAG-GTTA-3' (SEQ ID NO:11)/5'-CACTCTGCCGT-TCTCTTTCC-3' (SEQ ID NO:12)). The thermocycling was conducted for 35 cycles with annealing temperature of 65° C.

The amplicons were digested with XbaI enzyme according to the manufacturer's instructions and the digest was separated on a 4% agarose gel. The presence of XbaI polymorphism within the intron 7 of the mucine 4 gene corresponds to the presence of F4ac/ab receptor. A single band of 367 bp is indicative for homozygous (RR) resistant piglets, three bands of 367 bp, 216 bp and 151 bp represent heterozygous (RS) susceptible piglets, while two bands of 216 bp and 151 bp represent homozygous (SS) susceptible piglets.

In Vivo Feed-Challenge Experiment

In Vivo Experimental Feed Formulation

The daily feed intake of piglets from the age of 4 to 6 weeks when housed in groups in a pen varies from 300-400 grams, and, in general, is low at 4 weeks of age and gradually increased. From the expression levels of respective antibodies in the two-seed oligomeric pools and taking into account that the piglets consume 300 grams of feed per day, the experimental feed dose was formulated.

The concentration of VHH-IgG antibody was 14 mg in every gram of crushed VHH-IgG *Arabidopsis* seed flour. Therefore, to formulate a dose 80 mg antibody per pig per day in VHH-IgG-80 feed, 5.71 grams of *Arabidopsis* flour was mixed in every 300 grams of basic piglet feed, i.e., at inclusion rate of 1.9%. Further, to dose 20 mg of VHH-IgG per pig, the same VHH-IgG *Arabidopsis* seed flour was added to basic feed at an inclusion rate of 0.48%. The VHH-IgA antibody concentration was 2 mg/gram of crushed *Arabidopsis* VHH-IgA flour. To dose 20 mg per pig per day, 10 gram of VHH-IgA *Arabidopsis* flour was mixed in every 300 grams of basic feed, i.e., at an inclusion rate of 3.3% (Table 2). The negative control group piglets received feed with 1.9% wild-type *Arabidopsis* seed flour (equivalent to VHH-IgG-80 feed). To maintain nutritive homogeneity, flax seed meal was added. The flax seed composition is relatively similar to *Arabidopsis*: about 41% fat, 20% crude protein, 28% crude fiber, 7.7% moisture and 3.4% crude ash (Morris, 2007). The feed VHH-IgA-20 contained the highest amount of *Arabidopsis* seeds. To equalize the nutritive content, flax seed meal was added to the other three experimental treatment feeds (Table 2). Additionally, to enable similar nutritional balance throughout the experiment, the piglets were fed with feed containing 3.3% crushed flax seeds (flax-feed) both before and after the challenge regimen.

TABLE 2

Experimental feed formulation of the 4 respective groups

| Groups | Dose | Number of piglets | Total feed prepared in kg | Proportion of *Arabidopsis* seeds in feed | Proportion of flax seeds in feed |
|---|---|---|---|---|---|
| VHH-IgG-80 | 80 mg/300 gram feed) | 7 pigs | 21.36 | 1.9% (0.40 Kg) | 1.4% (0.3 Kg) |
| Negative control | | 7 pigs | 21.36 | 1.9% (0.40 Kg) | 1.4% (0.29 kg) |
| VHH-IgA-20 | (20 mg/300 gram feed) | 4 pigs | 15.3 | 3.3% (0.50 Kg) | n.a. |
| VHH-IgG-20 | (20 mg/300 gram feed) | 3 pigs | 10.5 | 0.48% (0.05 kg) | 2.82% (0.3 kg) |

(n.a. stands for not applicable)

Challenge Strain and Bacterial Inoculum

A pathogenic derivative from *e. coli* strain GIS 26 (0149: K91:F4ac, LT+, STa+, STb+) (Cox and Houvenaghel, 1993) was isolated to facilitate the screening of the pathogen post-infection. The streptomycin resistance of the strain was raised stepwise until 1 mg/ml of medium, by progressive screening for bacterial colonies that grew on higher dose of streptomycin. Prior to infection, the presence of all the toxin genes in this streptomycin-resistant strain was confirmed by PCR. The expression of F4 fimbriae and its potential to attach to F4R was confirmed by an in vitro adhesion test and this strain was named $GIS26R^{strep}$. One day before challenge, the challenge inoculum was prepared with $GIS26R^{strep}$ as described previously (Snoeck et al., 2003), Briefly, a single colony was inoculated in Tryptone Soya Broth (Oxoid, Basingstoke, UK) and cultured overnight at 37° C. The bacteria were collected by centrifugation (2000 g, 35 minutes at 40° C.) and resuspended in PBS (pH 7.4) to an optical density of 1 at 660 nm, corresponding to $10^9$ bacteria/ml (Snoeck et al., 2003).

Experimental Set Up and Feeding Regime

All the experimental procedures involving piglets and their maintenance was in accordance with the Belgian legislation for animal welfare and were approved by the animal care and ethics committee of the Gent University, Belgium.

Figure 10:
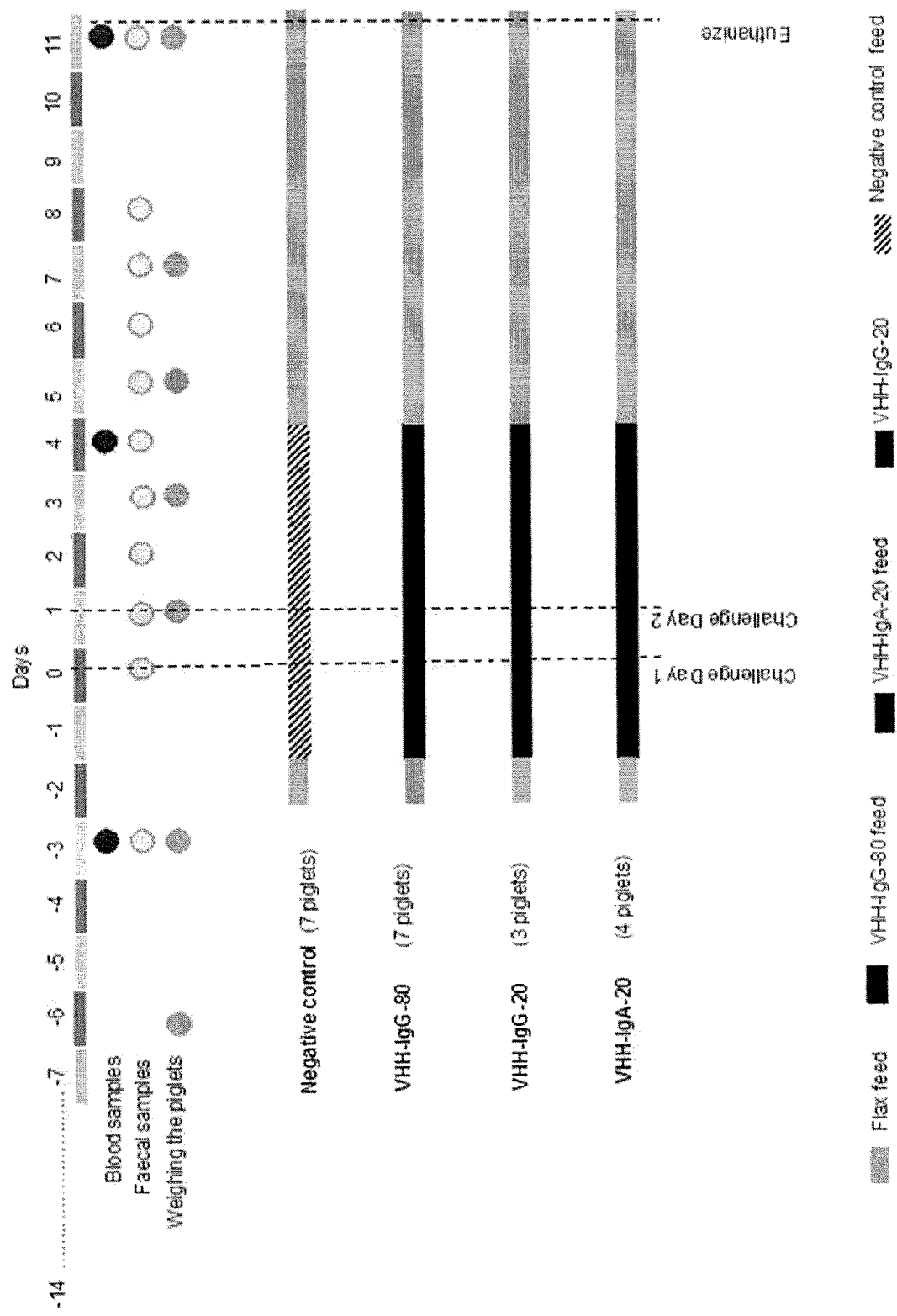
FIG. 10: Schematic representation of the in vivo experiment.

Hundred suckling piglets raised in a conventional Belgian porcine farm (Belgian Landrace×English Landrace) were screened, of which 21 piglets from four litters, seronegative for anti-F4+ETEC antibody and heterozygous for F4R receptor gene (genotype-RS) were selected for the feed-challenge experiment. The piglets were challenged twice (day 0 and day 1 of the time line, FIG. 10). On the day −14, at 3 weeks of age, the piglets were weaned and brought to the laboratory stables where they were housed together for 8 days (day −14 to −7) in one pen at 24±2° C. Water and starter flax feed containing 2 g colistin per kg of flax feed and was available ad libitum.

On the day −6, all the piglets were weighed, given ear tag number from 1 to 21 and separated into four pens, respectively, into each of the four experimental feed-treatment groups. Within these pens, water was provided ad libitum while the experimental feed was limited to 350 grams daily per pig. The feed was given in the four common feeding units installed in each pen. The negative control group (NC) included seven piglets (piglet numbers 1-7) and received feed with milled wild-type *Arabidopsis* seed (feed-NC). Another group of seven piglets, numbers 8 to 14, constituted the "VHH-IgG-80" group, receiving the VHH-IgG-80 feed, average daily consumption of this feed leads to a dose of 80 mg of VHH-IgG per pig per day. Piglets 15, 16 and 17 comprised the VHH-IgG-20 group and received a low dose of IgG treatment in feed VHH-IgG-20, daily dietary allowance of this feed formulation corresponded to ~20 mg of VHH-IgG per pig per day. The remaining four piglets (numbers 18 to 21) received VHH-IgA-20 feed comprising an oligomeric cocktail of VHH-IgA antibodies, also at a concentration of ~20 mg dose per pig per day. This experimental feed with milled *Arabidopsis* seeds was fed from the day −6 until day 4 of the experiment, except day −2 when all piglets were given basal flax feed. After day 4, the feed in each pen was switched to flax-feed, which was then provided ad libitum until day 11 when the piglets were euthanized by injecting an overdose of NEMBUTAL® (sedative anesthetic compound) (60 mg/kg body weight) (see schematic representation, FIG. 10).

To reduce the bacterial gut flora before the challenge, a broad spectrum antibiotic mix of 1 ml florfenicol (NU-FLOR®) and 2.5 mg/kg body weight of BAYTRIL® (Enrofloxacin (antimicrobial, Bayer)) in 5 ml of PBS was orally administered on days −6 and −5, and 150,000 U/kg of colistin was administered orally on day −3. On day 0 and day 1, the piglets were challenged by intragastric inoculation of $10^{10}$ bacterial particles in accordance with the protocol described by Cox et al. (1991), with the exception that the piglets were not fasted or deprived of water both before and after the challenge. Briefly, the piglets were sedated with 2 ml Azaperone (STRESSNILL® Janssen Animal Health) and the gastric pH was neutralized with 60 ml of $NaHCO_3$ (1.4% w/v in distilled water) administered via intubation. After 15-30 minutes, 10 ml challenge bacterial suspension in PBS ($10^9$ bacteria/ml) was inoculated by intubation. During the course of the experiment, the weight gain was evaluated by measuring the body weight on day −6, −3, 1, 3, 5, 7 and 11. Blood samples were taken from the jugular vein on days −3, 4, and day 11, while fecal samples were taken from the anus (or through rectum) on day −3, days 0 to 8 and day 11. After euthanizing, the piglets were dissected; the content from ileum and caecum was taken and processed similarly as the feces sample. A 20 cm long segment of the jejunum was excised, washed with sufficient PBS followed by Kreb's buffer and fixed by incubation for 60 minutes in Kreb's buffer with formaldehyde (1% v/v). The villous enterocytes were scrapped from this segment and used to reconfirm the phenotypic expression of the F4R receptors via an adhesion assay.

Determination of F4+ETEC Shedding in Feces

The feces samples were kept on ice and processed immediately. The cold chain was maintained until plating of the fecal dilution. First, a 10% (w/v) fecal suspension was made in PBS, and serially diluted to $1 \times 10^{-5}$. One hundred μl of each dilution was plated with glass beads on blood-agar plates (OXOID) with 1 mg/ml streptomycin, 20 μg/ml of tetracycline and 10% v/v defibrinated sheep blood (Bio-Trading). The plates were incubated at 37° C. overnight, and the hemolytic F4+ETEC bacteria were counted. The bacterial count was confirmed by colony blotting where a circular PVDF membrane is activated in methanol and then placed on the colonies in the Petri plates for 2 hours at room temperature. The blots were then blocked in blocking solution (5% skimmed milk in PBS) overnight at 4° C.; subsequently the blots were washed three times in PBS and incubated in a 3% skimmed milk in PBS bath with anti-F4-HRP (monoclonal antibody isolated in Lab of Immunology, UGent) for 1 hour at room temperature. The blots were washed again three times with PBS and developed with AEC (3-Amino-9-ethylcarbazole) (Sigma) substrate according to the manufacturers' instructions. After 15 minutes of incubation with the substrate, the membranes were washed with water and the precipitated colored dots specifically representing F4+ETEC were counted.

Figure 11:
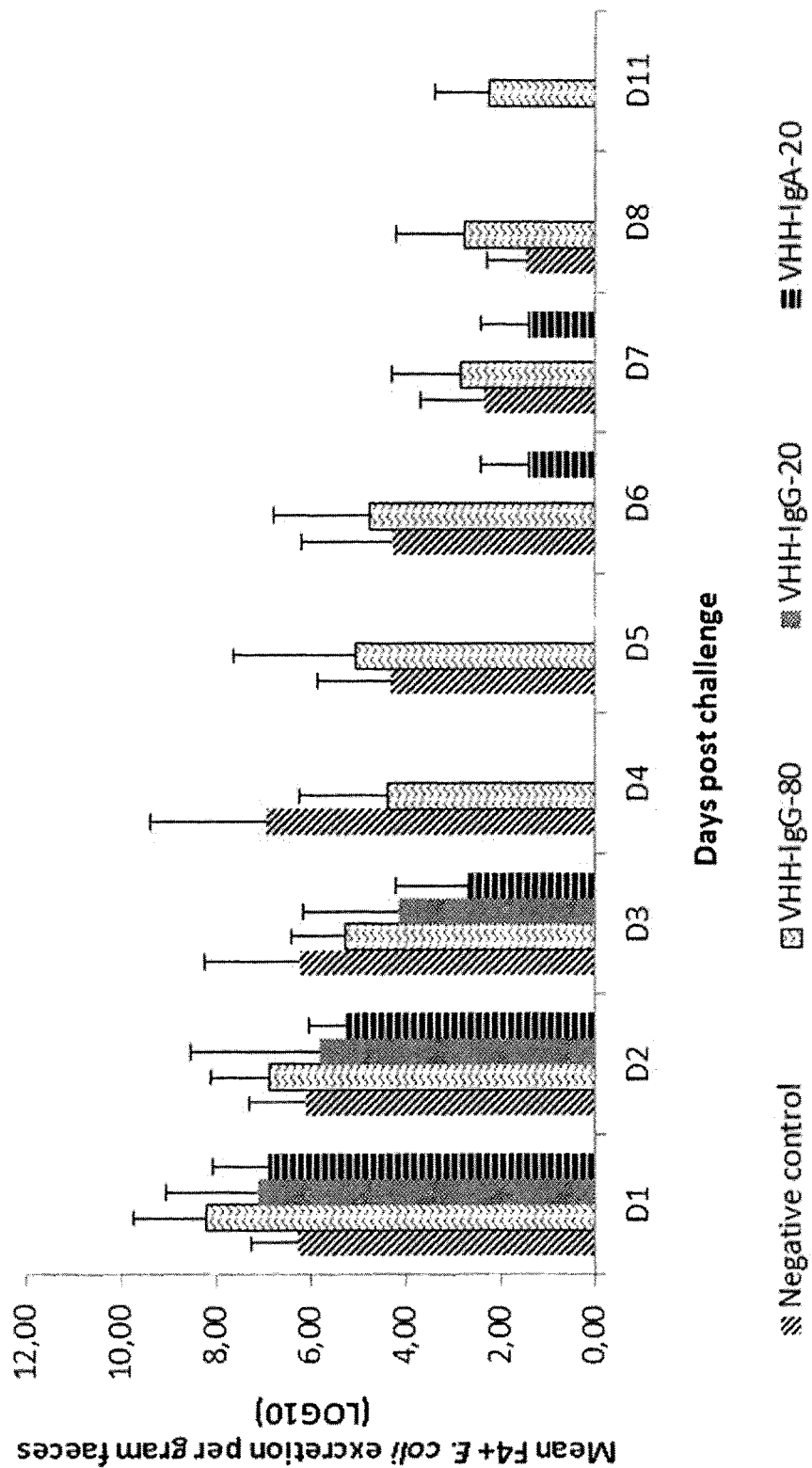
FIG. 11: In the group fed with feed supplemented with seeds containing VHH-IgA, the bacterial shedding rapidly decreased post-experimental infection as compared to other groups fed with feed supplemented with wild-type seeds or supplemented with seeds containing VHH-IgG. The error bars represent standard deviation within the group. The evolution of bacterial shedding in the course of time within the group VHH-IgG-80, VHH-IgA-20 and the Negative control group was significant (p=0.019).

All the piglets shed high titers of the challenged F4+ETEC strain immediately after the first day of challenge. The negative control group on an average shed bacteria higher than $1 \times 10^6$ cfu/ml per gram of feces until day 4, after which the bacterial shedding gradually declined until day 8 (FIG. 11).

Maintenance of the high shedding in the initial period is indicative for bacterial multiplication in the gut and possible colonization in the small intestine. The shedding gradually declined over time. In contrast to the negative control group, the bacterial infection was inhibited in the VHH-IgA treated group, as immediately after the challenge the bacterial shedding rapidly decreased below detection level of less than 100 bacteria per gram of feces (FIG. 11).

A similar rapid clearance of the bacteria by day 4 after challenge was also seen in the VHH-IgG-20 group, but not in VHH-IgG-80 group. The shedding profile observed for the VHH-IgG-80 group showed maintenance of a high infection pressure, and clearly indicates that the VHH-IgG at 80 mg dose per day failed to protect the piglets (FIG. 11). The prolonged higher rate of shedding as compared to negative control suggests that the VHH-IgG treatment at the dose of 80 mg per day was detrimental and synergistic for F4+ETEC infection, rather than protective.

Although these results suggests that an equivalent dose of 20 mg of VHH-IgG (divalent) is equally effective in bacterial clearance as 20 mg of VHH-IgA (FIG. 11), the quantitative determination of the F4R status performed postmortem by villi binding test, revealed that out of three piglets in this group (VHH-IgG-20), two had very few F4 receptors. Piglets with no or relative absence of F4 receptors are known to be naturally insensitive to F4+ETEC infection and such piglets shed very low bacteria and are protected even on experimental challenge (Geenen et al., 2004; Geenen et al., 2007). This situation within the VHH-IgG-20 group led to an overall diminished infection pressure in the pen since two out of three piglets were relatively insensitive to F4+ETEC infection.

Piglets in the other group on an average had moderate expression of F4R. In the four piglets of the VHH-IgA-20 group, approximately 32±8 bacteria adhering per 250 μm of the villous surface were observed ruling out the possibility of a F4 receptor negative status. In case of the third treatment group VHH-IgG-80, the seven piglets had an average of 27±6 bacteria attached per 250 μm of the villous surface. Also, the negative control group on an average had moderate expression of F4R. Thus, except for the VHH-IgG-20 group, the receptor-positive status of the piglets achieved a high infection pressure.

IgG as candidate for passive immunization has been suggested for decades. Humanized IgG antibodies for intravenous passive immunization are even clinically administered. Given the success of these intravenous IgG-based passive immunization therapy, it is often assumed that IgG that survive the gut would render similar protection. However, the negative results from the VHH-IgG-80 group contradict this hypothesis and indicate that IgG is not suitable for oral passive immunization. The faster seroconversion (FIG. 12), and prolonged bacterial shedding observed in this study, could be due to the innate interaction of porcine IgG3 Fc of the VHH-IgG construct with the porcine FcRn expressed in the gut. This FcRn-bound VHH-IgGs might have facilitated bacterial attachment and colonization.

Example 11: Seroprofile Corroborates Shedding Profile

Figure 12:
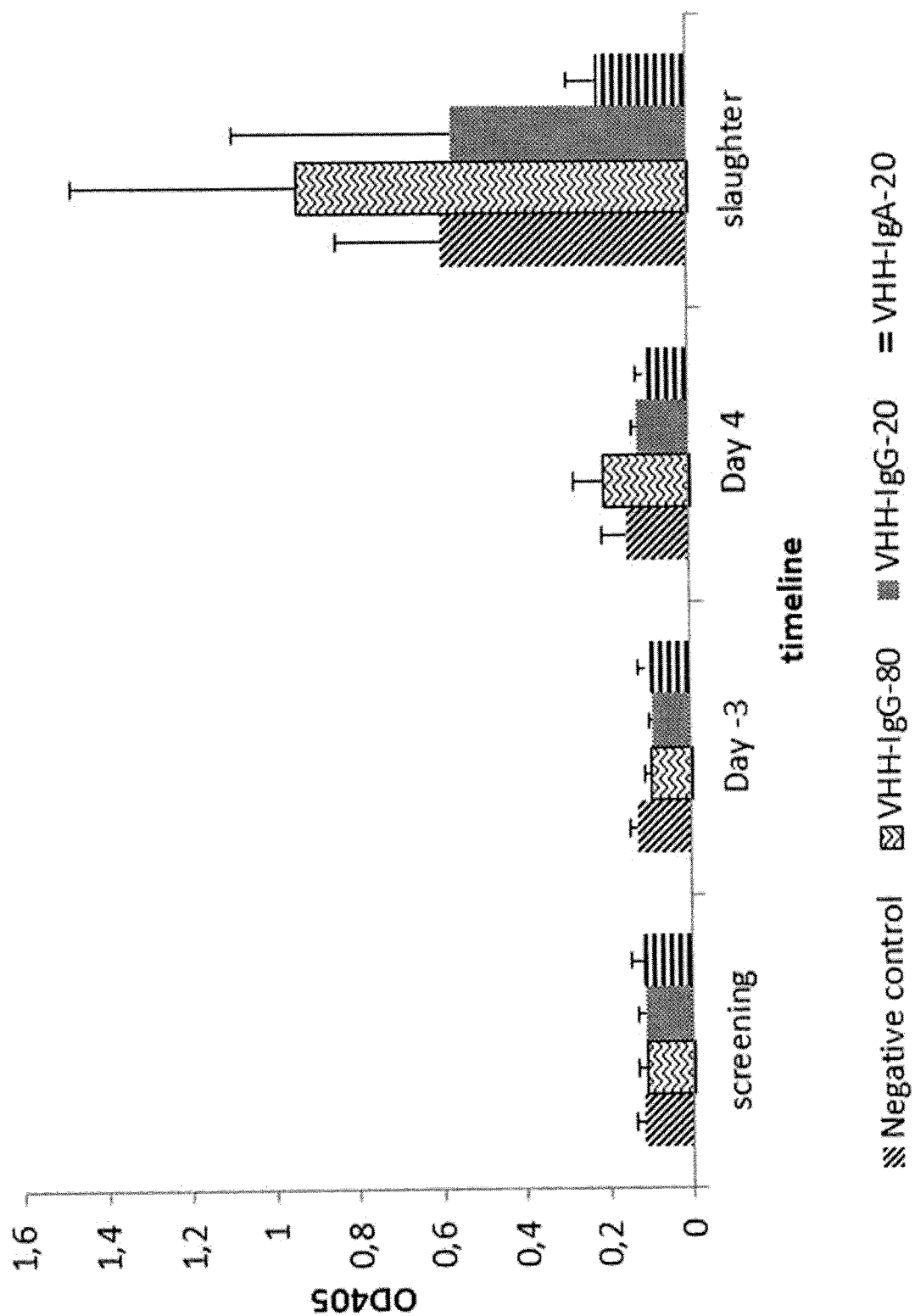
FIG. 12: Rate of seroconversion post-challenge in the four experimental groups: the bar represents an average of anti-F4 immunoglobulins in the blood of the animals within each group detected with anti-pig immunoglobulin polyclonal serum. The error bars represent standard deviation. The difference in rate of seroconversion evolution between the group VHH-IgG-80, VHH-IgA-20 and the negative control from the day of challenge (day 0) till the day of slaughter (day 11) was significant (p=0.003).
Figure 13:
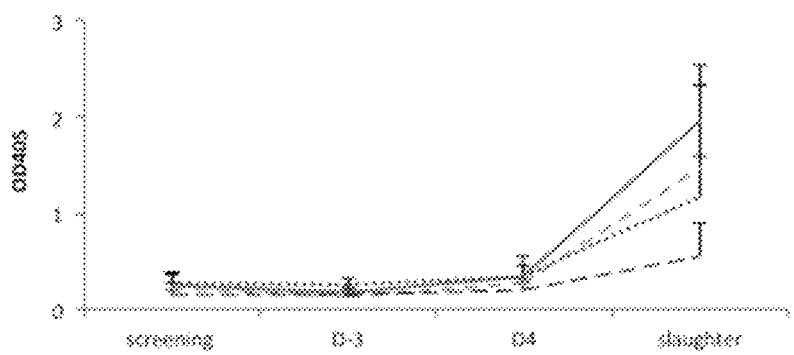
FIG. 13: Comparison of serum immunoglobulin isotype response post-F4+ETEC challenge in the four experimental groups over time. Challenges were given on day 0 and day 1. The earliest rise of serum IgM level was detected by day 4 in all piglets, indicative of F4+ETEC primary immune response. The serum IgG and IgA levels rose after day 4 as detected on day 11. The evolution of anti-F4-IgM between the group VHH-IgG-80, VHH-IgA-20 and the negative control from day 0 of challenge till the day of euthanasia, i.e., day 11, showed tendency of being significant, while the difference was significant at day 0 (p=0.044) and day 11 (p=0.025). The evolution of anti-F4-IgG, anti-F4-IgA between the group VHH-IgG-80, VHH-IgA-20 and the negative control from day 0 of challenge till the day they were euthanized on day 11 was significant (p=0.00 and p=0.01, respectively).
Figure 13:
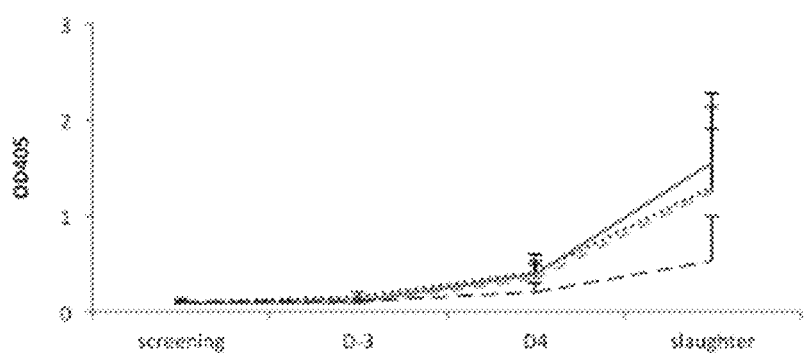
Figure 13:
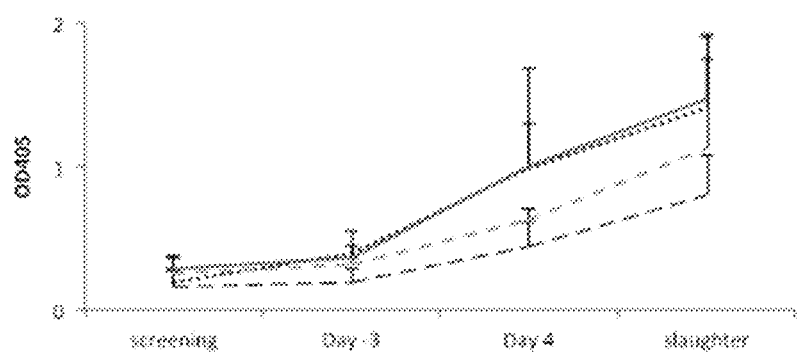

To determine the titer of anti-F4+ETEC antibodies in the serum, an ELISA setup was used. The overall shedding profile of each of the treatment groups correlated to the observed rise of anti-F4 fimbriae antibodies observed in the blood samples taken on day −3, day 4 and day 11 for each respective group (FIG. 12). The rise in serum IgM levels as early as 4 days post-challenge is an indication of the immune response to F4+ETEC bacteria. In agreement with previous studies, a high titer of serum anti-F4 fimbriae IgG was detected in serum collected from the negative control group and for both the VHH-IgG treatment groups on day 11 (FIG. 13). In comparison with these three groups, the evolution of immunoglobulin seroconversion rate observed for the four piglets in the VHH-IgA-20 group was much lower (FIG. 12). This suggests that the VHH-IgA antibodies at a 20 mg dose per day provided passive protection at the gut mucosal surface by preventing the interaction of the pathogenic bacteria with host cells and avoiding priming of the immune system.

Contrary to the VHH-IgA feed formulations, VHH-IgG-80 failed to achieve such passive protection. The overall higher titer of the VHH-IgG-80 group is due to the higher bacterial infection, which is corroborated by higher bacterial shedding in the group.

Example 12: Effect of the In-Feed Prophylaxis on the Weight Gain of Piglets

The pattern of bacterial shedding and the seroconversion rate are important parameters for assessing protection conferred by the in-feed produced anti-F4+ETEC antibody treatment. However, for the porcine industry, in addition to the efficacy of treatment, the piglet weight gain parameter is of utmost importance since it bears a direct relation to economic benefits. Piglets suffering from post-weaning diarrhea usually have a worse feed-to-weight conversion ratio, in comparison to healthy piglets.

Figure 14:
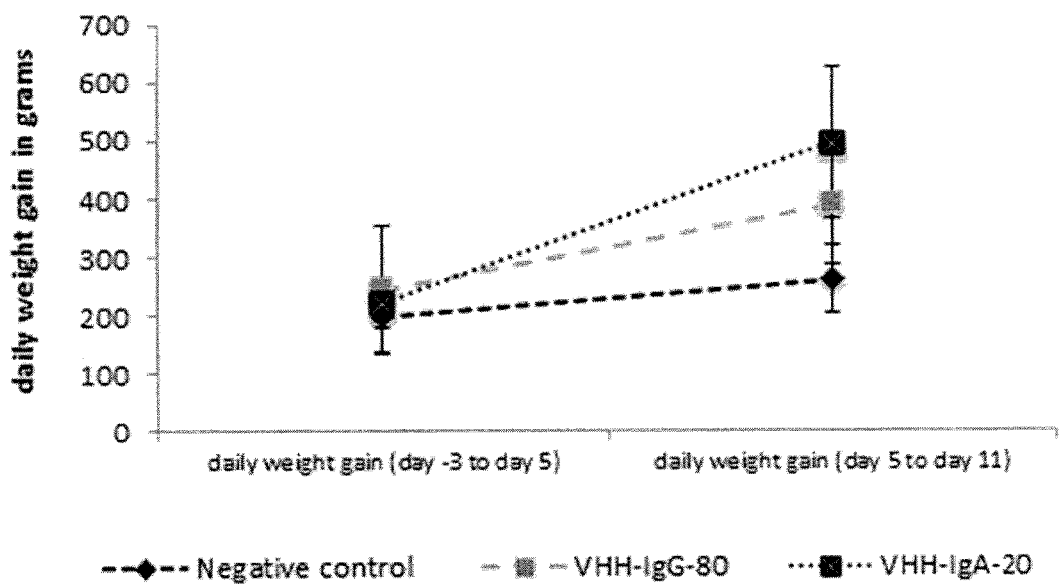
FIG. 14: Comparative weight gain during (day −3 to day 5) and after the experimental diet (day 5 to day 11) in the three groups. The bars represent standard deviation in weight gain from the average weight gain, calculated in grams. This observed evolution of weight gain for the three groups over time was highly significant (p=0.006).

In this study, it was found that the average weight gain for the negative control piglets (from day −3 to day 11) was low. On the contrary, the weight gain in all three experimental feed treatment groups was higher than the negative control (FIG. 14). The average weight gain was highest for the VHH-IgG-20 group and like the rapid bacterial clearance seen in this group, the weight gain could also be the effect of F4R-related insensitivity to F4+ETEC infection. Hence, except for this group, the daily weight gain of the remaining piglets in the three groups was calculated from the weight measured during the experiment (see scheme, FIG. 10).

The daily weight gain of all the piglets in the three groups (negative control, VHH-IgG-80 and VHH-IgA-20) around the challenge period while on Arabidopsis seed flour-containing diet was reasonably similar (day −3 to day 5). However, after changing this feed to containing the basal diet from day 5 to day 11, piglets previously on VHH-IgA-20 feed and VHH-IgG-80 feed had a higher daily weight gain, in comparison with the negative control (FIG. 14). Understandably, the high weight gain for the VHH-IgA-20 piglets can be associated to protection against F4+ETEC challenge conferred by the in-feed VHH-IgA antibodies. However, higher weight gain in the VHH-IgG-80 group, nudges for further evaluation of this group and the FcRn hypothesis.

Figure 15:
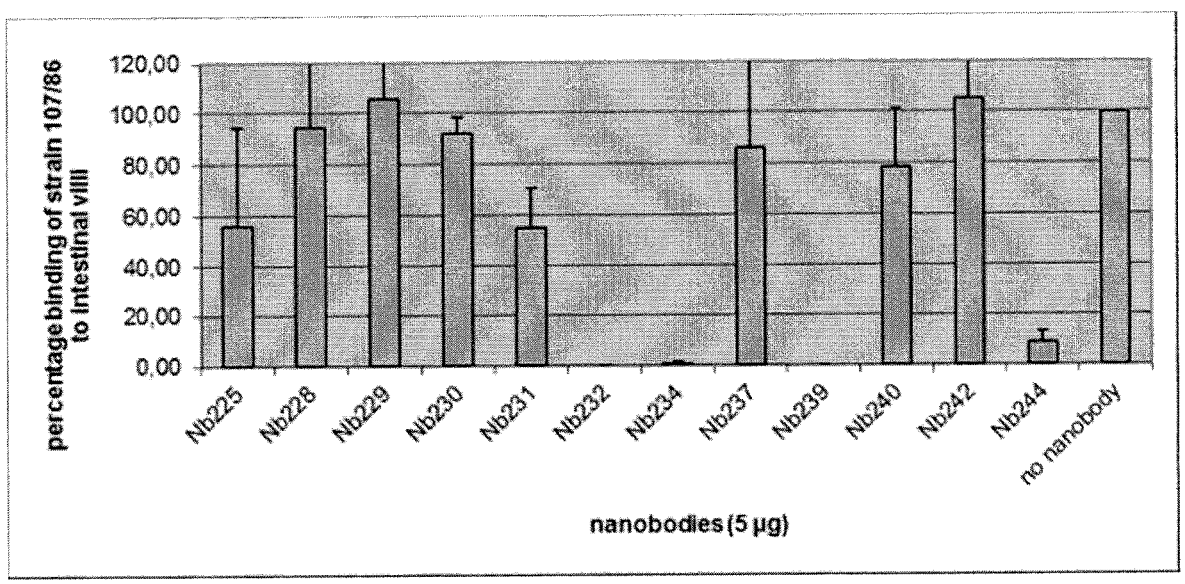
FIG. 15: In vitro adhesion inhibition of F18-positive *E. coli* strain 107/86 with purified monovalent nanobodies.

The VHH-IgG-80 feed though had a positive effect on weight gain; the average weight for the VHH-IgA-20 group still remains comparatively higher (FIG. 15). In field conditions, both in large-scale porcine farms as well as small-scale subsistence farming, the ability of a therapeutic feed to rapidly limit the bacterial shedding helps in decreasing the overall infection pressure within the herd. The VHH-IgA prophylaxis in this study showed signs of such reduction in overall infection pressure, making it ideal for large-scale prophylaxis in porcine farms to curtail any accidental outbreak of the highly contagious F4+ETEC bacteria.

In this study, it was demonstrated the potential of in-feed prophylaxis produced customized antibodies in preventing F4+ETEC infection and its positive effect on weight gain, which is promising for avoidance of economic losses to porcine industry. Further, production of these VHH-IgA antibodies in the seeds of crops like soybean, which can be bulk produced within the farming infrastructure, would enable cost-effective F4+ETEC therapeutic feed.

Example 13: In Vitro Adhesion Inhibition of F18 Positive E. coli by Anti-FedF Nanobodies Cloning, Expression, Purification and Characterization of FedF Lectin Domain In pigs, F18+ETEC and Shiga toxin producing E. coli (STEC) are responsible for causing post-weaning diarrhea and edema disease, respectively (Imberechts et al., 1994). F18 fimbriae are encoded by the fed gene cluster. This gene cluster is composed of five genes, encoding the major subunit FedA, the usher protein FedB, the periplasmic chaperone FedC, the minor pilin FedE and the tip adhesin FedF (Imberechts et al., 1996; Smeds et al., 2001). Recently, it was shown that the FedF adhesin of the F18 fimbriae is a two-domain adhesin (Moonens et al., 2012) and is responsible for binding to glycosphingolipids bearing blood group A/H determinants on type 1 core present as the host cell surface receptors (Coddens et al., 2009).

The first 165 residues of FedF adhesin (lectin domain FedF$_{15-165}$) from the F18-positive *E. coli* 107/86 strain (Bertschinger et al., 1990; Imberechts et al., 1996; gene accession No. Z26520) was cloned in the pDEST14 vector under the T7 promoter (Gateway Technology, Invitrogen). This lectin domain was purified from the *E. coli* periplasm as described (De Kerpel et al., 2006). The identity of the purified FedF$_{15-165}$ was confirmed in immunoblotting using a polyclonal rabbit antiserum raised against the his-tagged FedF$_{1-165H6}$ construct. This domain FedF was shown to fold into a defined, stable receptor-binding domain that binds specifically to ABH type 1 blood group glycans (Moonens et al., 2012). Directed mutagenesis and in vitro binding studies confirm the glycan-binding site identified in the N-terminal domain of FedF and this domain determines F18-mediated adhesion to pig enterocytes (Moonens et al., 2012).

Isolation of VHHs

Purified recombinant receptor-binding domain FedF$_{15-165}$ was used to immunize a healthy llama. The cDNA library construction, phage display and panning procedures were carried out according to the standard procedures. Independent FedF binding VHHs were selected by ELISA on plates coated with the purified FedF$_{15-165}$ recombinant domain. Colonies corresponding to VHHs giving a positive signal in the ELISA screen were further tested by amplifying the VHH gene. Identical VHHs were eliminated using restriction fragment length polymorphism analysis (RFLP). Finally, 17 different VHHs were retained after sequencing. From these 17, 12 VHHs were recloned under the control of the P$_{BAD}$ promoter and overexpressed in the WK6 strain after induction with arabinose (0.2% final concentration). The nanobodies (Nbs) encoded by these 12 VHH expression clones (pExp225, pExp228, pExp229, pExp230, pExp231, pExp232, pExp234, pExp237, pExp239, pExp240, pExp242 and pExp244) were purified from the periplasm using Ni-affinity chromatography. The binding of these 12 Nbs to the purified FedF$_{15-165}$ recombinant receptor-binding domain was confirmed by ELISA.

The purified monovalent nanobodies were tested for their ability to inhibit the in vitro adhesion assay on small intestinal villous enterocytes and was performed as described (Coddens et al., 2007). To 4×10$^8$ F18-positive 107/86 bacterial cells, 5 µg purified nanobody was added in a total volume of 500 µl phosphate buffered saline (PBS) and incubated for 1 hour at room temperature to allow the nanobody to bind to the FedF adhesin. It was then tested to see if the nanobody-pretreated bacterial cells were still binding to villi. Therefore, the nanobody-pretreated 4×10$^8$ bacterial cells were transferred to an average of 50 villi in a total volume of 500 µl PBS, followed by incubation at room temperature for 1 hour while being gently shaken. Villi were examined by phase-contrast microscopy at a magnification of 600× and the number of bacteria adhering along 50 µm brush border was quantitatively evaluated by counting the number of adhering bacteria at 20 randomly selected places, after which the mean bacterial adhesion was calculated. Adhesion tests were performed on intestinal villi of two different piglets.

As can be seen from FIG. 15, four nanobodies (Nb232, Nb234, Nb239 and Nb244 encoded by pExp232, pExp234, pExp239 and pExp244. respectively) out of 12 nanobodies are inhibiting the in vitro bacterial adhesion of F18-positive bacterial cells to intestinal villi.

REFERENCES

Aliprandi M., E. Sparacio, F. Pivetta, G. Ossolengo, R. Maestro, and A. de Marco (2010). The availability of recombinant anti-SNAP antibody in VHH format amplifies the application flexibility of SNAP-tagged proteins. *J. Biomed Biotech*, Volume 2010, Article ID 658954.

Amezcua R., R. M. Friendship, C. E. Dewey, C. Gyles and J. M. Fairbrother (2002). Presentation of post-weaning *Escherichia coli* diarrhea in southern Ontario, prevalence of hemolytic *E. coli* serogroups involved, and their antimicrobial resistance patterns. *Canadian Journal of Veterinary Research—Revue Canadienne De Recherche Veterinaire* 66, 73-78.

Bendtsen J. D., H. Nielsen, G. von Heijne, and S. Brunak (2004). Improved prediction of signal peptides: SignalP 3.0. *Journal Mol. Biol.* 340, 783-795.

Bertschinger H. U., M. Bachmann, C. Mettler, A. Pospischil, E. M. Schraner, M. Stamm, T. Sydler, and P. Wild (1990). Adhesive fimbriae produced in vivo by *Escherichia coli* 0139:K12(B):H1 associated with enterotoxaemia in pigs. *Vet. Microbiol.* 25:267-281.

Clough S. J. and A. F. Bent (1998). Floral dip: a simplified method for *Agrobacterium*-mediated transformation of *Arabidopsis thaliana*. *Plant J.* 16, 735-743.

Coddens A., F. Verdonck, P. Tiels, K. Rasschaert, B. M. Goddeeris, and E. Cox (2007). The age-dependent expression of the F18+*E. coli* receptor on porcine gut epithelial cells is positively correlated with the presence of histo-blood group antigens. *Vet. Microbiol.* 122:332-341.

Coddens A., M. Diswall, J. Angstrom, M. E. Breimer, B. Goddeeris, E. Cox, and S. Teneberg (2009). Recognition of Blood Group ABH Type 1 Determinants by the FedF Adhesin of F18-fimbriated *Escherichia coli*. *Journal of Biological Chemistry* 284, 9713-9726.

Cox E., E. Schrauwen, V. Cools, and A. Houvenaghel (1991). "Experimental Induction of Diarrhea in Newly-Weaned Piglets." *J. Vet. Med. Ser. A—Zentbl Vet. Med. Reihe. A—Physiol. Pathol. Clin. Med.* 38, 418-426.

Cox E. and A. Houvenaghel (1993). Comparison of the in vitro adhesion of K88, K99, F41 and P987 positive *Escherichia coli* to intestinal villi of 4- to 5-week-old pigs. *Vet. Microbiol.* 34, 7-18.

De Buck S., V. Virdi, T. De Meyer, K. De Wilde, R. Piron, J. Nolf, E. Van Lerberge, E. De Paepe, and A. Depicker (eds) (2011). *Production of camel-like antibodies in plants*. New York: Springer.

de Geus B., M. Harmsen, and F. van Zijderveld (1998). Prevention of diarrhea using pathogen-specific monoclonal antibodies in an experimental enterotoxigenic *E. coli* infection in germfree piglets. *Vet. Q.* 20, S87-S89.

De Kerpel M., I. Van Molle, L. Brys, L. Wyns, H. De Greve, and J. Bouckaert (2006). N-terminal truncation enables crystallization of the receptor-binding domain of the FedF bacterial adhesin. *Acta. Crystallogr. Sect. F. Struct. Biol. Cryst. Commun.* 62: 1278-1282.

Fairbrother J. M., E. Nadeau and C. L. Gyles (2005). *Escherichia coli* in post-weaning diarrhea in pigs: an update of bacterial types, pathogenesis and preventions strategies. *Anim. Health Res. Rev.* 6, 17-39.

Geenen P. L., J. Van der Meulen, A. Bouma and M. C. M. De Jong (2004). Estimating transmission parameters of F4+*E. coli* for F4-receptor-positive and -negative piglets: one-to-one transmission experiment. *Epidemiol. Infect.* 132, 1039-1048.

Geenen P. L., J. Van der Meulen, A. Bouma, B. Engel, J. A. P. Heesterbeek, and M. C. M. De Jong (2007). Classification of temporal profiles of F4+ *E. coli* shedding and fecal dry matter in experimental post-weaning diarrhea of pigs. *Epidemiol. Infect.* 135, 1001-1009.

Harmsen M. M., C. B. van Solt, A. Hoogendoorn, F. G. van Zijderveld, T. A. Niewold, and J. van der Meulen (2005). *Escherichia coli* F4 fimbriae-specific llama single-domain antibody fragments effectively inhibit bacterial adhesion in vitro but poorly protect against diarrhea. *Vet. Microbiol.* 111, 89-98.

Hood E. E., S. B. Gelvin, L. S. Melchers, and A. Hoekema (1993). New *Agrobacterium* helper plasmids for gene-transfer to plants. *Transgenic Res.* 2, 208-218.

Hood E. E., G. L. Helmer, R. T. Fraley, and M. D. Chilton (1986). The hypervirulence of *Agrobacterium tumefaciens* A281 is encoded in a region of pTiBo542 outside of T-DNA. *J. Bacteriol.* 168, 1291-1301.

Hong T. T. T., N. Q. Linh, B. Ogle, and J. E. Lindberg (2006). Survey on the prevalence of diarrhea in pre-weaning piglets and on feeding systems as contributing risk factors in smallholdings in Central Vietnam. *Tropical Animal Health and Production* 38, 397-405.

Imberechts H., H. U. Bertschinger, M. Stamm, T. Sydler, P. Pohl, H. De Greve, J. P. Hemalsteens, M. Van Montagu, and P. Lintermans (1994). Prevalence of F107 fimbriae on *Escherichia coli* isolated from pigs with edema disease or post-weaning diarrhea. *Vet. Microbiol.* 40, 219-230.

Imberechts H., P. Wild, G. Charlier, H. De Greve, P. Lintermans, and P. Pohl (1996). Characterization of F18 fimbrial genes fedE and fedF involved in adhesion and length of enterotoxemic *Escherichia coli* strain 107/86. *Microb. Pathog.* 21: 183-192.

Karnoup A. S., V. Turkelson, and W. H. Anderson (2005). 0-glycosylation in maize-expressed human IgA1. *Glycobiology* 15, 965-981.

Kapitani R. A. and E. J. Zebrowski (1973). A high resolution PAS stain for polyacrylamide gel electrophoresis. *Anal. Biochem.* 56, 361-369.

Karimi M., B. De Meyer, and P. Hilson (2005). Modular cloning in plant cells. *Trends Plant Sci.* 10, 103-105.

Kjan I., R. M. Twylan, E. Arcalis, and E. Stoger (2012). Using storage organelles for the accumulation and encapsulation of recombinant proteins. *Biotechnol. J.* 7, 1-11.

Madec F., N. Bridoux, S. Bounaix, R. Cariolet, Y. Duval-Iflah, D. J. Hampson, and A. Jestin (2000). Experimental models of porcine post-weaning colibacillosis and their relationship to post-weaning diarrhea and digestive disorders as encountered in the field. *Veterinary Microbiology* 72, 295-310.

Marquardt R. R., L. Z. Jin, J.-W. Kim, L. Fang, A. A. Frohlich, and S. K. Baidoo (1999). Passive protective effect of egg-yolk antibodies against enterotoxigenic *Escherichia coli* K88+ infection in neonatal and early-weaned piglets. *FEMS Immunology and Medical Microbiology* 23, 283-288.

Mikschofsky H., H. Schirrmeier, G. M. Keil, B. Lange, P. L. Polowick, W. Keller, and I. Broer (2009). Pea-derived vaccines demonstrate high immunogenicity and protection in rabbits against rabbit hemorrhagic disease virus. *Plant Biotechnol. J.* 7, 537-549.

Moonens K., J. Bouckaert, A. Coddens, T. Tran, S. Panjikar, M. De Kerpel, E. Cox, H. Remaut, and H. De Greve (2012). Structural insight in histo-blood group binding by the F18 fimbrial adhesin FedF. *Mol. Microbiol.* in press.

Morandini et al. (2011). Non-food/feed seeds as biofactories for the high yield production of recombinant pharmaceuticals. *Plant Biotech. J.* 9, 911-921.

Morris D. H. (2007). *Flax—A Health and Nutrition Primer*. Canada: Flax council of Canada.

Murashige T. and F. Skoog (1962). A revised medium for rapid growth and bio assays with tobacco tissue cultures. *Physiol. Plant* 15, 473-497.

Niewold T. A., A. J. van Dijk, P. L. Geenen, H. Roodink, R. Margry, and J. van der Meulen (2007). Dietary-specific antibodies in spray-dried immune plasma prevent enterotoxigenic *Escherichia coli* F4 (ETEC) post-weaning diarrhea in piglets. *Veterinary Microbiology* 124, 362-369.

Paz M. M., H. X. Shou, Z. B. Guo, Z. Y. Zhang, A. K. Banerjee, and K. Wang (2004). Assessment of conditions affecting *Agrobacterium*-mediated soybean transformation using the cotyledonary node explant. *Euphytica* 136, 167-179.

Polowick P. L., J. Quandt, and J. D. Mahon (2000). The ability of pea transformation technology to transfer genes into peas adapted to western Canadian growing conditions. *Plant Sci.* 153, 161-170.

Rasschaert K., F. Verdonck, B. M. Goddeeris, L. Duchateau, and E. Cox (2007). Screening of pigs resistant to F4 enterotoxigenic *Escherichia coli* (ETEC) infection. *Veterinary Microbiology* 123, 249-253.

Reilly R. M., R. Domingo, and J. Sandhu (1997). Oral delivery of antibodies—Future pharmacokinetic trends. *Clinical Pharmacokinetics* 32, 313-323.

Riising H. J., M. Murmans, and M. Witvliet (2005). Protection Against Neonatal *Escherichia coli* Diarrhea in Pigs by Vaccination of Sows with a New Vaccine that Contains Purified Enterotoxic *E. coli* Virulence Factors F4ac, F4ab, F5 and F6 Fimbrial Antigens and Heat-Labile *E. coli* Enterotoxin (LT) Toxoid. *Journal of Veterinary Medicine*, Series B 52, 296-300.

Smeds A., K. Hemmann, M. Jakava-Viljanen, S. Pelkonen, H. Imberechts, and A. Palva (2001). Characterization of the adhesin of *Escherichia coli* F18 fimbriae. *Infect. Immun.* 69: 7941-7945.

Snoeck V., N. Huyghebaert, E. Cox, A. Vermeire, S. Vancaeneghem, J. P. Remon, and B. M. Goddeeris (2003). Enteric-coated pellets of F4 fimbriae for oral vaccination of suckling piglets against enterotoxigenic *Escherichia coli* infections. *Vet. Immunol. Immunopathol.* 96, 219-227.

Vanlandschoot P., C. Stortelers, E. Beirnaert, L. I. Ibanez, B. Schepens, E. Depla, and X. Saelens (2011). NANOBODIES®: New ammunition to battle viruses. *Antiviral Res.* 92, 389-407.

Wilson M. R. and J. Svendsen (1971). Immunity to *Escherichia coli* in pigs. The role of milk in protective immunity to *E. coli* enteritis. *Canadian Journal of Comparative Medicine* 35, 239-243.

Yokoyama H., R. C. Peralta, R. Diaz, S. Sendo, Y. Ikemori, and Y. Kodama (1992). Passive protective effect of chicken egg yolk immunoglobulins against experimental enterotoxigenic *Escherichia coli* infection in neonatal piglets. *Infect. Immun.* 60, 998-1007.

The invention claimed is:

1. A fusion protein comprising an anti-Enterotoxigenic *Escherichia coli* (anti-ETEC) antigen-binding heavy chain variable domain of a camelid heavy-chain antibody (VHH) fused to an IgA Fc domain;
    wherein the anti-ETEC VHH was identified by a method comprising:
        selecting a VHH that specifically binds to Enterotoxigenic *Escherichia coli* in a screening assay.

2. The fusion protein according to claim 1, wherein said anti-ETEC VHH is selected from the group consisting of an anti-F4+ETEC VHH and an anti-F18+ETEC VHH.

3. The fusion protein according to claim 2, wherein said anti-ETEC VHH is specific for the FaeG domain of *E. coli* F4 fimbriae.

4. The fusion protein according to claim 2, wherein said anti-ETEC VHH is specific for the FedF domain of *E. coli* F18 fimbriae.

5. The fusion protein of claim 1, wherein said IgA is a porcine IgA.

6. The fusion protein according to claim 5, wherein said porcine IgA is IgAb.

7. A protein complex comprising:
the fusion protein of claim 1; and
a J chain and/or a secretory component chain.

8. A method of treating a subject suffering from or at risk of suffering from enterotoxigenic *Escherichia coli* (ETEC) infection, the method comprising:
administering the fusion protein of claim 1 to the subject thereby treating the ETEC infection or the risk of suffering from ETEC infection.

9. A fusion protein comprising an anti-Enterotoxigenic *Escherichia coli* (anti-ETEC) antigen-binding heavy chain variable domain of a camelid heavy-chain antibody (VHH) fused to an IgA Fc domain;
wherein the VHH is comprised in a protein selected from the group consisting of SEQ ID NO:2, SEQ ID NO:4, SEQ ID NO:6, and SEQ ID NO:8.

10. A fusion protein comprising an anti-Enterotoxigenic *Escherichia coli* (anti-ETEC) antigen-binding heavy chain variable domain of a camelid heavy-chain antibody (VHH) fused to an IgA Fc domain, wherein said fusion protein inhibits adhesion of ETEC to gut villous enterocytes.

11. A fusion protein comprising an anti-Enterotoxigenic *Escherichia coli* (anti-ETEC) antigen-binding heavy chain variable domain of a camelid heavy-chain antibody (VHH) fused to an IgA Fc domain, wherein said anti-ETEC VHH is an anti-F4+ETEC VHH.

\* \* \* \* \*

SEQUENCE LISTING

<160> NUMBER OF SEQ ID NOS: 12

<210> SEQ ID NO 1
<211> LENGTH: 1092
<212> TYPE: DNA
<213> ORGANISM: Artificial Sequence
<220> FEATURE:
<223> OTHER INFORMATION: Fusion construct V1A
<220> FEATURE:
<221> NAME/KEY: CDS
<222> LOCATION: (1)..(1092)

<400> SEQUENCE: 1

| | | | | | | | | | | | | | | | | |
|---|---|---|---|---|---|---|---|---|---|---|---|---|---|---|---|---|
| cag | gtg | cag | ctg | cag | gag | tct | gga | gga | ggc | ttg | gtg | cag | gct | ggg | ggg | 48 |
| Gln | Val | Gln | Leu | Gln | Glu | Ser | Gly | Gly | Gly | Leu | Val | Gln | Ala | Gly | Gly | |
| 1 | | | | 5 | | | | | 10 | | | | | 15 | | |

| tct | ctg | aga | ctc | tcc | tgt | gaa | gcc | tct | gga | aat | gtc | gac | aga | atc | gat | 96 |
|---|---|---|---|---|---|---|---|---|---|---|---|---|---|---|---|---|
| Ser | Leu | Arg | Leu | Ser | Cys | Glu | Ala | Ser | Gly | Asn | Val | Asp | Arg | Ile | Asp | |
| | | | 20 | | | | | 25 | | | | | 30 | | | |

| gcc | atg | ggc | tgg | ttc | cgc | cag | gct | cca | ggg | aaa | cag | cgc | gag | ttc | gtt | 144 |
|---|---|---|---|---|---|---|---|---|---|---|---|---|---|---|---|---|
| Ala | Met | Gly | Trp | Phe | Arg | Gln | Ala | Pro | Gly | Lys | Gln | Arg | Glu | Phe | Val | |
| | | 35 | | | | | 40 | | | | | 45 | | | | |

| ggt | tat | att | agt | gaa | ggt | ggt | ata | tta | aac | tat | gga | gac | ttt | gtg | aag | 192 |
|---|---|---|---|---|---|---|---|---|---|---|---|---|---|---|---|---|
| Gly | Tyr | Ile | Ser | Glu | Gly | Gly | Ile | Leu | Asn | Tyr | Gly | Asp | Phe | Val | Lys | |
| 50 | | | | | 55 | | | | | 60 | | | | | | |

| ggc | cga | ttc | acc | atc | tcc | aga | gac | aac | gcc | aag | aat | acg | gtg | tat | ctg | 240 |
|---|---|---|---|---|---|---|---|---|---|---|---|---|---|---|---|---|
| Gly | Arg | Phe | Thr | Ile | Ser | Arg | Asp | Asn | Ala | Lys | Asn | Thr | Val | Tyr | Leu | |
| 65 | | | | | 70 | | | | | 75 | | | | | 80 | |

| caa | atg | agc | aac | ctg | aaa | tct | gag | gac | aca | ggc | gtc | tat | ttt | tgt | gca | 288 |
|---|---|---|---|---|---|---|---|---|---|---|---|---|---|---|---|---|
| Gln | Met | Ser | Asn | Leu | Lys | Ser | Glu | Asp | Thr | Gly | Val | Tyr | Phe | Cys | Ala | |
| | | | | 85 | | | | | 90 | | | | | 95 | | |

| gct | agc | cat | tgg | gga | aca | cta | ctt | atc | aag | gga | ata | gaa | cac | tgg | ggc | 336 |
|---|---|---|---|---|---|---|---|---|---|---|---|---|---|---|---|---|
| Ala | Ser | His | Trp | Gly | Thr | Leu | Leu | Ile | Lys | Gly | Ile | Glu | His | Trp | Gly | |
| | | | 100 | | | | | 105 | | | | | 110 | | | |

| aaa | ggc | acc | cag | gtc | acc | gtc | tcc | tca | gat | cca | tgt | cct | cag | tgc | tgc | 384 |
|---|---|---|---|---|---|---|---|---|---|---|---|---|---|---|---|---|
| Lys | Gly | Thr | Gln | Val | Thr | Val | Ser | Ser | Asp | Pro | Cys | Pro | Gln | Cys | Cys | |
| | | 115 | | | | | 120 | | | | | 125 | | | | |

| aag | ccc | agc | ttg | tcc | ttg | cag | cca | cca | gct | ctt | gca | gac | ctc | ctc | ctc | 432 |
|---|---|---|---|---|---|---|---|---|---|---|---|---|---|---|---|---|
| Lys | Pro | Ser | Leu | Ser | Leu | Gln | Pro | Pro | Ala | Leu | Ala | Asp | Leu | Leu | Leu | |
| | 130 | | | | | 135 | | | | | 140 | | | | | |

| gga | tca | aat | gcc | agc | ctc | acc | tgc | aca | ctc | agt | gga | ctc | aaa | aaa | tca | 480 |
|---|---|---|---|---|---|---|---|---|---|---|---|---|---|---|---|---|
| Gly | Ser | Asn | Ala | Ser | Leu | Thr | Cys | Thr | Leu | Ser | Gly | Leu | Lys | Lys | Ser | |
| 145 | | | | | 150 | | | | | 155 | | | | | 160 | |

| gag | ggt | gtc | agc | ttc | act | tgg | caa | ccc | tca | ggt | ggg | aag | gat | gct | gtc | 528 |
|---|---|---|---|---|---|---|---|---|---|---|---|---|---|---|---|---|
| Glu | Gly | Val | Ser | Phe | Thr | Trp | Gln | Pro | Ser | Gly | Gly | Lys | Asp | Ala | Val | |
| | | | | 165 | | | | | 170 | | | | | 175 | | |

| caa | gcg | tcc | ccc | acg | cgt | gat | tca | tgt | ggc | tgc | tac | agc | gtt | tcc | agc | 576 |
|---|---|---|---|---|---|---|---|---|---|---|---|---|---|---|---|---|
| Gln | Ala | Ser | Pro | Thr | Arg | Asp | Ser | Cys | Gly | Cys | Tyr | Ser | Val | Ser | Ser | |
| | | | 180 | | | | | 185 | | | | | 190 | | | |

| att | ttg | cca | ggc | tgt | gct | gat | cct | tgg | aac | aaa | gga | gaa | aca | ttt | tcc | 624 |
|---|---|---|---|---|---|---|---|---|---|---|---|---|---|---|---|---|
| Ile | Leu | Pro | Gly | Cys | Ala | Asp | Pro | Trp | Asn | Lys | Gly | Glu | Thr | Phe | Ser | |
| | | 195 | | | | | 200 | | | | | 205 | | | | |

| tgc | acc | gct | gcc | cac | tct | gag | ttg | aag | agc | gcg | cta | acc | gct | acc | atc | 672 |
|---|---|---|---|---|---|---|---|---|---|---|---|---|---|---|---|---|
| Cys | Thr | Ala | Ala | His | Ser | Glu | Leu | Lys | Ser | Ala | Leu | Thr | Ala | Thr | Ile | |
| 210 | | | | | 215 | | | | | 220 | | | | | | |

| act | aaa | cct | aaa | gtt | aac | acg | ttc | aga | ccc | caa | gtc | cac | ttg | ttg | ccg | 720 |
|---|---|---|---|---|---|---|---|---|---|---|---|---|---|---|---|---|
| Thr | Lys | Pro | Lys | Val | Asn | Thr | Phe | Arg | Pro | Gln | Val | His | Leu | Leu | Pro | |
| 225 | | | | | 230 | | | | | 235 | | | | | 240 | |

| ccg | ccg | tcg | gag | gag | ctc | gct | ctc | aac | gaa | ctc | gtt | aca | ctc | aca | tgc | 768 |
|---|---|---|---|---|---|---|---|---|---|---|---|---|---|---|---|---|
| Pro | Pro | Ser | Glu | Glu | Leu | Ala | Leu | Asn | Glu | Leu | Val | Thr | Leu | Thr | Cys | |
| | | | | 245 | | | | | 250 | | | | | 255 | | |

```
ctc gta aga ggc ttt agc cct aag gat gtg tta gtt cga tgg ctg caa     816
Leu Val Arg Gly Phe Ser Pro Lys Asp Val Leu Val Arg Trp Leu Gln
            260                 265                 270 ggg ggc caa gaa ttg ccc cgt gac aag tac ctc gtc tgg gaa tcc ctt     864
Gly Gly Gln Glu Leu Pro Arg Asp Lys Tyr Leu Val Trp Glu Ser Leu
        275                 280                 285 cca gaa cct gga cag gct atc ccc acc tac gcc gtt acc agc gtg ctt     912
Pro Glu Pro Gly Gln Ala Ile Pro Thr Tyr Ala Val Thr Ser Val Leu
    290                 295                 300 cgc gtt gac gcc gaa gac tgg aag cag gga gac acc ttc tcc tgc atg     960
Arg Val Asp Ala Glu Asp Trp Lys Gln Gly Asp Thr Phe Ser Cys Met
305                 310                 315                 320 gta gga cac gag gct cta cct ctt gcc ttc acc cag aag acc atc gac    1008
Val Gly His Glu Ala Leu Pro Leu Ala Phe Thr Gln Lys Thr Ile Asp
                325                 330                 335 cgc ctt gcg ggt aaa ccc acc cac gtc aac gtg tca gtt gtc atg gcg    1056
Arg Leu Ala Gly Lys Pro Thr His Val Asn Val Ser Val Val Met Ala
            340                 345                 350 gag gca gaa ggc ata tgc tac aaa gac gag ctt taa                    1092
Glu Ala Glu Gly Ile Cys Tyr Lys Asp Glu Leu
        355                 360
```

<210> SEQ ID NO 2
<211> LENGTH: 363
<212> TYPE: PRT
<213> ORGANISM: Artificial Sequence
<220> FEATURE:
<223> OTHER INFORMATION: Synthetic Construct

<400> SEQUENCE: 2

```
Gln Val Gln Leu Gln Glu Ser Gly Gly Gly Leu Val Gln Ala Gly Gly
1               5                   10                  15

Ser Leu Arg Leu Ser Cys Glu Ala Ser Gly Asn Val Asp Arg Ile Asp
            20                  25                  30

Ala Met Gly Trp Phe Arg Gln Ala Pro Gly Lys Gln Arg Glu Phe Val
        35                  40                  45

Gly Tyr Ile Ser Glu Gly Gly Ile Leu Asn Tyr Gly Asp Phe Val Lys
    50                  55                  60

Gly Arg Phe Thr Ile Ser Arg Asp Asn Ala Lys Asn Thr Val Tyr Leu
65                  70                  75                  80

Gln Met Ser Asn Leu Lys Ser Glu Asp Thr Gly Val Tyr Phe Cys Ala
                85                  90                  95

Ala Ser His Trp Gly Thr Leu Leu Ile Lys Gly Ile Glu His Trp Gly
            100                 105                 110

Lys Gly Thr Gln Val Thr Val Ser Ser Asp Pro Cys Pro Gln Cys Cys
        115                 120                 125

Lys Pro Ser Leu Ser Leu Gln Pro Pro Ala Leu Ala Asp Leu Leu Leu
    130                 135                 140

Gly Ser Asn Ala Ser Leu Thr Cys Thr Leu Ser Gly Leu Lys Lys Ser
145                 150                 155                 160

Glu Gly Val Ser Phe Thr Trp Gln Pro Ser Gly Lys Asp Ala Val
                165                 170                 175

Gln Ala Ser Pro Thr Arg Asp Ser Cys Gly Cys Tyr Ser Val Ser Ser
            180                 185                 190

Ile Leu Pro Gly Cys Ala Asp Pro Trp Asn Lys Gly Glu Thr Phe Ser
        195                 200                 205

Cys Thr Ala Ala His Ser Glu Leu Lys Ser Ala Leu Thr Ala Thr Ile
    210                 215                 220
```

```
Thr Lys Pro Lys Val Asn Thr Phe Arg Pro Gln Val His Leu Leu Pro
225                 230                 235                 240

Pro Pro Ser Glu Glu Leu Ala Leu Asn Glu Leu Val Thr Leu Thr Cys
            245                 250                 255

Leu Val Arg Gly Phe Ser Pro Lys Asp Val Leu Val Arg Trp Leu Gln
        260                 265                 270

Gly Gly Gln Glu Leu Pro Arg Asp Lys Tyr Leu Val Trp Glu Ser Leu
    275                 280                 285

Pro Glu Pro Gly Gln Ala Ile Pro Thr Tyr Ala Val Thr Ser Val Leu
290                 295                 300

Arg Val Asp Ala Glu Asp Trp Lys Gln Gly Asp Thr Phe Ser Cys Met
305                 310                 315                 320

Val Gly His Glu Ala Leu Pro Leu Ala Phe Thr Gln Lys Thr Ile Asp
            325                 330                 335

Arg Leu Ala Gly Lys Pro Thr His Val Asn Val Ser Val Val Met Ala
        340                 345                 350

Glu Ala Glu Gly Ile Cys Tyr Lys Asp Glu Leu
    355                 360

<210> SEQ ID NO 3
<211> LENGTH: 1092
<212> TYPE: DNA
<213> ORGANISM: Artificial Sequence
<220> FEATURE:
<223> OTHER INFORMATION: Fusion construct V2A
<220> FEATURE:
<221> NAME/KEY: CDS
<222> LOCATION: (1)..(1092)

<400> SEQUENCE: 3 cag gtg cag ctg cag gag tct gga gga ggc ttg gtg cag cct ggg ggg      48
Gln Val Gln Leu Gln Glu Ser Gly Gly Gly Leu Val Gln Pro Gly Gly
1               5                   10                  15 tct ctg aga ctc tcc tgt aca gcc tcc gga agc atc tcc agt atc aat      96
Ser Leu Arg Leu Ser Cys Thr Ala Ser Gly Ser Ile Ser Ser Ile Asn
            20                  25                  30 gcc atg ggc tgg tac cgc cag gct cca ggg agc aag cgc gag ttc gtc     144
Ala Met Gly Trp Tyr Arg Gln Ala Pro Gly Ser Lys Arg Glu Phe Val
        35                  40                  45 gca cat att act aac acg ggt gtg aca gaa ttt gca gac tcc gtg aag     192
Ala His Ile Thr Asn Thr Gly Val Thr Glu Phe Ala Asp Ser Val Lys
    50                  55                  60 ggc cga ttc acc atc tcc aga gac aac gcc aag acc acg gtg gat ctg     240
Gly Arg Phe Thr Ile Ser Arg Asp Asn Ala Lys Thr Thr Val Asp Leu
65                  70                  75                  80 caa atg aac agc ctg aaa cct gag gac aca gcc gtc tat tac tgt gca     288
Gln Met Asn Ser Leu Lys Pro Glu Asp Thr Ala Val Tyr Tyr Cys Ala
            85                  90                  95 gct act gat tgg ggc acc cta ctt atc aag ggc att gac cac tgg ggt     336
Ala Thr Asp Trp Gly Thr Leu Leu Ile Lys Gly Ile Asp His Trp Gly
        100                 105                 110 aaa ggg acc cag gtc acc gtc tcc tca gat cca tgt cct cag tgc tgc     384
Lys Gly Thr Gln Val Thr Val Ser Ser Asp Pro Cys Pro Gln Cys Cys
    115                 120                 125 aag ccc agc ttg tcc ttg cag cca cca gct ctt gca gac ctc ctc ctc     432
Lys Pro Ser Leu Ser Leu Gln Pro Pro Ala Leu Ala Asp Leu Leu Leu
130                 135                 140 gga tca aat gcc agc ctc acc tgc aca ctc agt gga ctc aaa aaa tca     480
Gly Ser Asn Ala Ser Leu Thr Cys Thr Leu Ser Gly Leu Lys Lys Ser
```

```
                    145                 150                 155                 160
gag ggt gtc agc ttc act tgg caa ccc tca ggt ggg aag gat gct gtc           528
Glu Gly Val Ser Phe Thr Trp Gln Pro Ser Gly Gly Lys Asp Ala Val
                165                 170                 175 caa gcg tcc ccc acg cgt gat tca tgt ggc tgc tac agc gtt tcc agc           576
Gln Ala Ser Pro Thr Arg Asp Ser Cys Gly Cys Tyr Ser Val Ser Ser
            180                 185                 190 att ttg cca ggc tgt gct gat cct tgg aac aaa gga gaa aca ttt tcc           624
Ile Leu Pro Gly Cys Ala Asp Pro Trp Asn Lys Gly Glu Thr Phe Ser
        195                 200                 205 tgc acc gct gcc cac tct gag ttg aag agc gcg cta acc gct acc atc           672
Cys Thr Ala Ala His Ser Glu Leu Lys Ser Ala Leu Thr Ala Thr Ile
    210                 215                 220 act aaa cct aaa gtt aac acg ttc aga ccc caa gtc cac ttg ttg ccg           720
Thr Lys Pro Lys Val Asn Thr Phe Arg Pro Gln Val His Leu Leu Pro
225                 230                 235                 240 ccg ccg tcg gag gag ctc gct ctc aac gaa ctc gtt aca ctc aca tgc           768
Pro Pro Ser Glu Glu Leu Ala Leu Asn Glu Leu Val Thr Leu Thr Cys
                245                 250                 255 ctc gta aga ggc ttt agc cct aag gat gtg tta gtt cga tgg ctg caa           816
Leu Val Arg Gly Phe Ser Pro Lys Asp Val Leu Val Arg Trp Leu Gln
            260                 265                 270 ggg ggc caa gaa ttg ccc cgt gac aag tac ctc gtc tgg gaa tcc ctt           864
Gly Gly Gln Glu Leu Pro Arg Asp Lys Tyr Leu Val Trp Glu Ser Leu
        275                 280                 285 cca gaa cct gga cag gct atc ccc acc tac gcc gtt acc agc gtg ctt           912
Pro Glu Pro Gly Gln Ala Ile Pro Thr Tyr Ala Val Thr Ser Val Leu
    290                 295                 300 cgc gtt gac gcc gaa gac tgg aag cag gga gac acc ttc tcc tgc atg           960
Arg Val Asp Ala Glu Asp Trp Lys Gln Gly Asp Thr Phe Ser Cys Met
305                 310                 315                 320 gta gga cac gag gct cta cct ctt gcc ttc acc cag aag acc atc gac          1008
Val Gly His Glu Ala Leu Pro Leu Ala Phe Thr Gln Lys Thr Ile Asp
                325                 330                 335 cgc ctt gcg ggt aaa ccc acc cac gtc aac gtg tca gtt gtc atg gcg          1056
Arg Leu Ala Gly Lys Pro Thr His Val Asn Val Ser Val Val Met Ala
            340                 345                 350 gag gca gaa ggc ata tgc tac aaa gac gag ctt taa                          1092
Glu Ala Glu Gly Ile Cys Tyr Lys Asp Glu Leu
        355                 360

<210> SEQ ID NO 4
<211> LENGTH: 363
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Gln Glu Ser Gly Gly Gly Leu Val Gln Pro Gly Gly
1               5                   10                  15

Ser Leu Arg Leu Ser Cys Thr Ala Ser Gly Ser Ile Ser Ser Ile Asn
            20                  25                  30

Ala Met Gly Trp Tyr Arg Gln Ala Pro Gly Ser Lys Arg Glu Phe Val
        35                  40                  45

Ala His Ile Thr Asn Thr Gly Val Thr Glu Phe Ala Asp Ser Val Lys
    50                  55                  60

Gly Arg Phe Thr Ile Ser Arg Asp Asn Ala Lys Thr Thr Val Asp Leu
65                  70                  75                  80
```

```
Gln Met Asn Ser Leu Lys Pro Glu Asp Thr Ala Val Tyr Tyr Cys Ala
                85                  90                  95
Ala Thr Asp Trp Gly Thr Leu Leu Ile Lys Gly Ile Asp His Trp Gly
            100                 105                 110
Lys Gly Thr Gln Val Thr Val Ser Ser Asp Pro Cys Pro Gln Cys Cys
        115                 120                 125
Lys Pro Ser Leu Ser Leu Gln Pro Pro Ala Leu Ala Asp Leu Leu Leu
    130                 135                 140
Gly Ser Asn Ala Ser Leu Thr Cys Thr Leu Ser Gly Leu Lys Lys Ser
145                 150                 155                 160
Glu Gly Val Ser Phe Thr Trp Gln Pro Ser Gly Gly Lys Asp Ala Val
                165                 170                 175
Gln Ala Ser Pro Thr Arg Asp Ser Cys Gly Cys Tyr Ser Val Ser Ser
            180                 185                 190
Ile Leu Pro Gly Cys Ala Asp Pro Trp Asn Lys Gly Glu Thr Phe Ser
        195                 200                 205
Cys Thr Ala Ala His Ser Glu Leu Lys Ser Ala Leu Thr Ala Thr Ile
    210                 215                 220
Thr Lys Pro Lys Val Asn Thr Phe Arg Pro Gln Val His Leu Leu Pro
225                 230                 235                 240
Pro Pro Ser Glu Glu Leu Ala Leu Asn Glu Leu Val Thr Leu Thr Cys
                245                 250                 255
Leu Val Arg Gly Phe Ser Pro Lys Asp Val Leu Val Arg Trp Leu Gln
            260                 265                 270
Gly Gly Gln Glu Leu Pro Arg Asp Lys Tyr Leu Val Trp Glu Ser Leu
        275                 280                 285
Pro Glu Pro Gly Gln Ala Ile Pro Thr Tyr Ala Val Thr Ser Val Leu
    290                 295                 300
Arg Val Asp Ala Glu Asp Trp Lys Gln Gly Asp Thr Phe Ser Cys Met
305                 310                 315                 320
Val Gly His Glu Ala Leu Pro Leu Ala Phe Thr Gln Lys Thr Ile Asp
                325                 330                 335
Arg Leu Ala Gly Lys Pro Thr His Val Asn Val Ser Val Val Met Ala
            340                 345                 350
Glu Ala Glu Gly Ile Cys Tyr Lys Asp Glu Leu
        355                 360

<210> SEQ ID NO 5
<211> LENGTH: 1092
<212> TYPE: DNA
<213> ORGANISM: Artificial Sequence
<220> FEATURE:
<223> OTHER INFORMATION: Fusion construct V3A
<220> FEATURE:
<221> NAME/KEY: CDS
<222> LOCATION: (1)..(1092)

<400> SEQUENCE: 5 cag gtg cag ctg cag gag tct gga gga ggc ttg gtg cag gct ggg ggg        48
Gln Val Gln Leu Gln Glu Ser Gly Gly Gly Leu Val Gln Ala Gly Gly
1               5                   10                  15 tct ctg aga ctc tcc tgt gca gcc tcg ggc ctt acc ttc gat act tat        96
Ser Leu Arg Leu Ser Cys Ala Ala Ser Gly Leu Thr Phe Asp Thr Tyr
            20                  25                  30 gcc atg ggc tgg ttc cgc cag gct cca ggg aag aag cgt gag tat gta       144
Ala Met Gly Trp Phe Arg Gln Ala Pro Gly Lys Lys Arg Glu Tyr Val
        35                  40                  45
```

-continued

| | | |
|---|---|---|
| gca gct att agc tgg acc ggt att agc aca tat tat gca gac atc gcg<br>Ala Ala Ile Ser Trp Thr Gly Ile Ser Thr Tyr Tyr Ala Asp Ile Ala<br>50                       55                      60 | | 192 |
| aag ggc cga ttc acc atc tcc aga gac aac gcc aag aac acg ctg tat<br>Lys Gly Arg Phe Thr Ile Ser Arg Asp Asn Ala Lys Asn Thr Leu Tyr<br>65                       70                     75                   80 | | 240 |
| cta caa atg gat agc ctg aaa cct gag gac acg gcc gtt tat tac tgt<br>Leu Gln Met Asp Ser Leu Lys Pro Glu Asp Thr Ala Val Tyr Tyr Cys<br>                     85                     90                     95 | | 288 |
| gca gcc caa aaa tcc ctc aac gta cca gcg ccg tgg gac tat tgg ggc<br>Ala Ala Gln Lys Ser Leu Asn Val Pro Ala Pro Trp Asp Tyr Trp Gly<br>100                     105                   110 | | 336 |
| cag ggg acc cag gtc acc gtc tcc tca gat cca tgt cct cag tgc tgc<br>Gln Gly Thr Gln Val Thr Val Ser Ser Asp Pro Cys Pro Gln Cys Cys<br>      115                   120                   125 | | 384 |
| aag ccc agc ttg tcc ttg cag cca cca gct ctt gca gac ctc ctc ctc<br>Lys Pro Ser Leu Ser Leu Gln Pro Pro Ala Leu Ala Asp Leu Leu Leu<br>130                     135                   140 | | 432 |
| gga tca aat gcc agc ctc acc tgc aca ctc agt gga ctc aaa aaa tca<br>Gly Ser Asn Ala Ser Leu Thr Cys Thr Leu Ser Gly Leu Lys Lys Ser<br>145                     150                   155                   160 | | 480 |
| gag ggt gtc agc ttc act tgg caa ccc tca ggt ggg aag gat gct gtc<br>Glu Gly Val Ser Phe Thr Trp Gln Pro Ser Gly Gly Lys Asp Ala Val<br>                 165                   170                   175 | | 528 |
| caa gcg tcc ccc acg cgt gat tca tgt ggc tgc tac agc gtt tcc agc<br>Gln Ala Ser Pro Thr Arg Asp Ser Cys Gly Cys Tyr Ser Val Ser Ser<br>            180                   185                   190 | | 576 |
| att ttg cca ggc tgt gct gat cct tgg aac aaa gga gaa aca ttt tcc<br>Ile Leu Pro Gly Cys Ala Asp Pro Trp Asn Lys Gly Glu Thr Phe Ser<br>                 195                   200                   205 | | 624 |
| tgc acc gct gcc cac tct gag ttg aag agc gcg cta acc gct acc atc<br>Cys Thr Ala Ala His Ser Glu Leu Lys Ser Ala Leu Thr Ala Thr Ile<br>210                     215                   220 | | 672 |
| act aaa cct aaa gtt aac acg ttc aga ccc caa gtc cac ttg ttg ccg<br>Thr Lys Pro Lys Val Asn Thr Phe Arg Pro Gln Val His Leu Leu Pro<br>225                     230                   235                   240 | | 720 |
| ccg ccg tcg gag gag ctc gct ctc aac gaa ctc gtt aca ctc aca tgc<br>Pro Pro Ser Glu Glu Leu Ala Leu Asn Glu Leu Val Thr Leu Thr Cys<br>                 245                   250                   255 | | 768 |
| ctc gta aga ggc ttt agc cct aag gat gtg tta gtt cga tgg ctg caa<br>Leu Val Arg Gly Phe Ser Pro Lys Asp Val Leu Val Arg Trp Leu Gln<br>      260                   265                   270 | | 816 |
| ggg ggc caa gaa ttg ccc cgt gac aag tac ctc gtc tgg gaa tcc ctt<br>Gly Gly Gln Glu Leu Pro Arg Asp Lys Tyr Leu Val Trp Glu Ser Leu<br>275                     280                   285 | | 864 |
| cca gaa cct gga cag gct atc ccc acc tac gcc gtt acc agc gtg ctt<br>Pro Glu Pro Gly Gln Ala Ile Pro Thr Tyr Ala Val Thr Ser Val Leu<br>290                     295                   300 | | 912 |
| cgc gtt gac gcc gaa gac tgg aag cag gga gac acc ttc tcc tgc atg<br>Arg Val Asp Ala Glu Asp Trp Lys Gln Gly Asp Thr Phe Ser Cys Met<br>305                     310                   315                   320 | | 960 |
| gta gga cac gag gct cta cct ctt gcc ttc acc cag aag acc atc gac<br>Val Gly His Glu Ala Leu Pro Leu Ala Phe Thr Gln Lys Thr Ile Asp<br>                 325                   330                   335 | | 1008 |
| cgc ctt gcg ggt aaa ccc acc cac gtc aac gtg tca gtt gtc atg gcg<br>Arg Leu Ala Gly Lys Pro Thr His Val Asn Val Ser Val Val Met Ala<br>            340                   345                   350 | | 1056 |
| gag gca gaa ggc ata tgc tac aaa gac gag ctt taa<br>Glu Ala Glu Gly Ile Cys Tyr Lys Asp Glu Leu<br>355                     360 | | 1092 |

<210> SEQ ID NO 6
<211> LENGTH: 363
<212> TYPE: PRT
<213> ORGANISM: Artificial Sequence
<220> FEATURE:
<223> OTHER INFORMATION: Synthetic Construct

<400> SEQUENCE: 6

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Leu Thr Phe Asp Thr Tyr
            20                  25                  30

Ala Met Gly Trp Phe Arg Gln Ala Pro Gly Lys Lys Arg Glu Tyr Val
        35                  40                  45

Ala Ala Ile Ser Trp Thr Gly Ile Ser Thr Tyr Tyr Ala Asp Ile Ala
    50                  55                  60

Lys Gly Arg Phe Thr Ile Ser Arg Asp Asn Ala Lys Asn Thr Leu Tyr
65                  70                  75                  80

Leu Gln Met Asp Ser Leu Lys Pro Glu Asp Thr Ala Val Tyr Tyr Cys
                85                  90                  95

Ala Ala Gln Lys Ser Leu Asn Val Pro Ala Pro Trp Asp Tyr Trp Gly
            100                 105                 110

Gln Gly Thr Gln Val Thr Val Ser Ser Asp Pro Cys Pro Gln Cys Cys
        115                 120                 125

Lys Pro Ser Leu Ser Leu Gln Pro Pro Ala Leu Ala Asp Leu Leu Leu
    130                 135                 140

Gly Ser Asn Ala Ser Leu Thr Cys Thr Leu Ser Gly Leu Lys Lys Ser
145                 150                 155                 160

Glu Gly Val Ser Phe Thr Trp Gln Pro Ser Gly Gly Lys Asp Ala Val
                165                 170                 175

Gln Ala Ser Pro Thr Arg Asp Ser Cys Gly Cys Tyr Ser Val Ser Ser
            180                 185                 190

Ile Leu Pro Gly Cys Ala Asp Pro Trp Asn Lys Gly Glu Thr Phe Ser
        195                 200                 205

Cys Thr Ala Ala His Ser Glu Leu Lys Ser Ala Leu Thr Ala Thr Ile
    210                 215                 220

Thr Lys Pro Lys Val Asn Thr Phe Arg Pro Gln Val His Leu Leu Pro
225                 230                 235                 240

Pro Pro Ser Glu Glu Leu Ala Leu Asn Glu Leu Val Thr Leu Thr Cys
                245                 250                 255

Leu Val Arg Gly Phe Ser Pro Lys Asp Val Leu Val Arg Trp Leu Gln
            260                 265                 270

Gly Gly Gln Glu Leu Pro Arg Asp Lys Tyr Leu Val Trp Glu Ser Leu
        275                 280                 285

Pro Glu Pro Gly Gln Ala Ile Pro Thr Tyr Ala Val Thr Ser Val Leu
    290                 295                 300

Arg Val Asp Ala Glu Asp Trp Lys Gln Gly Asp Thr Phe Ser Cys Met
305                 310                 315                 320

Val Gly His Glu Ala Leu Pro Leu Ala Phe Thr Gln Lys Thr Ile Asp
                325                 330                 335

Arg Leu Ala Gly Lys Pro Thr His Val Asn Val Ser Val Val Met Ala
            340                 345                 350

Glu Ala Glu Gly Ile Cys Tyr Lys Asp Glu Leu
        355                 360
```

<210> SEQ ID NO 7
<211> LENGTH: 1092
<212> TYPE: DNA
<213> ORGANISM: Artificial Sequence
<220> FEATURE:
<223> OTHER INFORMATION: Fusion construct V4A
<220> FEATURE:
<221> NAME/KEY: CDS
<222> LOCATION: (1)..(1092)

<400> SEQUENCE: 7

| | | | | | | | | | | | | | | | | |
|---|---|---|---|---|---|---|---|---|---|---|---|---|---|---|---|---|
| cag | gtg | cag | ctg | cag | gag | tct | gga | gga | gga | ttg | gtg | cag | gct | ggg | ggc | 48 |
| Gln | Val | Gln | Leu | Gln | Glu | Ser | Gly | Gly | Gly | Leu | Val | Gln | Ala | Gly | Gly | |
| 1 | | | | 5 | | | | | 10 | | | | | 15 | | |
| tct | ctg | aga | ctc | tcc | tgt | gca | gcc | tcg | ggc | ctt | acc | ttc | gat | act | tat | 96 |
| Ser | Leu | Arg | Leu | Ser | Cys | Ala | Ala | Ser | Gly | Leu | Thr | Phe | Asp | Thr | Tyr | |
| | | | 20 | | | | | 25 | | | | | 30 | | | |
| gcc | atg | ggc | tgg | ttc | cgc | cag | gct | cca | ggg | aag | aag | cgt | gag | tat | gta | 144 |
| Ala | Met | Gly | Trp | Phe | Arg | Gln | Ala | Pro | Gly | Lys | Lys | Arg | Glu | Tyr | Val | |
| | | 35 | | | | | 40 | | | | | 45 | | | | |
| gca | gcg | att | agc | tgg | acc | ggt | att | agc | aca | tat | tat | gca | gac | atc | gcg | 192 |
| Ala | Ala | Ile | Ser | Trp | Thr | Gly | Ile | Ser | Thr | Tyr | Tyr | Ala | Asp | Ile | Ala | |
| 50 | | | | | 55 | | | | | 60 | | | | | | |
| aag | ggc | cga | ttc | acc | atc | tcc | aga | gac | aac | gcc | aag | aac | acg | ctg | tat | 240 |
| Lys | Gly | Arg | Phe | Thr | Ile | Ser | Arg | Asp | Asn | Ala | Lys | Asn | Thr | Leu | Tyr | |
| 65 | | | | | 70 | | | | | 75 | | | | | 80 | |
| ctt | caa | atg | gac | agc | ctg | aaa | cct | gag | gac | acg | gcc | gtt | tat | tac | tgt | 288 |
| Leu | Gln | Met | Asp | Ser | Leu | Lys | Pro | Glu | Asp | Thr | Ala | Val | Tyr | Tyr | Cys | |
| | | | | 85 | | | | | 90 | | | | | 95 | | |
| gca | gcc | caa | aga | tcc | ctc | aac | gta | cca | gcg | ccg | tgg | gac | tat | tgg | ggc | 336 |
| Ala | Ala | Gln | Arg | Ser | Leu | Asn | Val | Pro | Ala | Pro | Trp | Asp | Tyr | Trp | Gly | |
| | | | | 100 | | | | | 105 | | | | | 110 | | |
| cag | ggg | acc | cag | gtc | acc | gtc | tcc | tca | gat | cca | tgt | cct | cag | tgc | tgc | 384 |
| Gln | Gly | Thr | Gln | Val | Thr | Val | Ser | Ser | Asp | Pro | Cys | Pro | Gln | Cys | Cys | |
| | | | 115 | | | | | 120 | | | | | 125 | | | |
| aag | ccc | agc | ttg | tcc | ttg | cag | cca | cca | gct | ctt | gca | gac | ctc | ctc | ctc | 432 |
| Lys | Pro | Ser | Leu | Ser | Leu | Gln | Pro | Pro | Ala | Leu | Ala | Asp | Leu | Leu | Leu | |
| | | 130 | | | | | 135 | | | | | 140 | | | | |
| gga | tca | aat | gcc | agc | ctc | acc | tgc | aca | ctc | agt | gga | ctc | aaa | aaa | tca | 480 |
| Gly | Ser | Asn | Ala | Ser | Leu | Thr | Cys | Thr | Leu | Ser | Gly | Leu | Lys | Lys | Ser | |
| 145 | | | | | 150 | | | | | 155 | | | | | 160 | |
| gag | ggt | gtc | agc | ttc | act | tgg | caa | ccc | tca | ggt | ggg | aag | gat | gct | gtc | 528 |
| Glu | Gly | Val | Ser | Phe | Thr | Trp | Gln | Pro | Ser | Gly | Gly | Lys | Asp | Ala | Val | |
| | | | | 165 | | | | | 170 | | | | | 175 | | |
| caa | gcg | tcc | ccc | acg | cgt | gat | tca | tgt | ggc | tgc | tac | agc | gtt | tcc | agc | 576 |
| Gln | Ala | Ser | Pro | Thr | Arg | Asp | Ser | Cys | Gly | Cys | Tyr | Ser | Val | Ser | Ser | |
| | | | | 180 | | | | | 185 | | | | | 190 | | |
| att | ttg | cca | ggc | tgt | gct | gat | cct | tgg | aac | aaa | gga | gaa | aca | ttt | tcc | 624 |
| Ile | Leu | Pro | Gly | Cys | Ala | Asp | Pro | Trp | Asn | Lys | Gly | Glu | Thr | Phe | Ser | |
| | | | 195 | | | | | 200 | | | | | 205 | | | |
| tgc | acc | gct | gcc | cac | tct | gag | ttg | aag | agc | gcg | cta | acc | gct | acc | atc | 672 |
| Cys | Thr | Ala | Ala | His | Ser | Glu | Leu | Lys | Ser | Ala | Leu | Thr | Ala | Thr | Ile | |
| | | 210 | | | | | 215 | | | | | 220 | | | | |
| act | aaa | cct | aaa | gtt | aac | acg | ttc | aga | ccc | caa | gtc | cac | ttg | ttg | ccg | 720 |
| Thr | Lys | Pro | Lys | Val | Asn | Thr | Phe | Arg | Pro | Gln | Val | His | Leu | Leu | Pro | |
| 225 | | | | | 230 | | | | | 235 | | | | | 240 | |
| ccg | ccg | tcg | gag | gag | ctc | gct | ctc | aac | gaa | ctc | gtt | aca | ctc | aca | tgc | 768 |
| Pro | Pro | Ser | Glu | Glu | Leu | Ala | Leu | Asn | Glu | Leu | Val | Thr | Leu | Thr | Cys | |
| | | | | 245 | | | | | 250 | | | | | 255 | | |
| ctc | gta | aga | ggc | ttt | agc | cct | aag | gat | gtg | tta | gtt | cga | tgg | ctg | caa | 816 |

```
Leu Val Arg Gly Phe Ser Pro Lys Asp Val Leu Val Arg Trp Leu Gln
            260                 265                 270 ggg ggc caa gaa ttg ccc cgt gac aag tac ctc gtc tgg gaa tcc ctt    864
Gly Gly Gln Glu Leu Pro Arg Asp Lys Tyr Leu Val Trp Glu Ser Leu
        275                 280                 285 cca gaa cct gga cag gct atc ccc acc tac gcc gtt acc agc gtg ctt    912
Pro Glu Pro Gly Gln Ala Ile Pro Thr Tyr Ala Val Thr Ser Val Leu
290                 295                 300 cgc gtt gac gcc gaa gac tgg aag cag gga gac acc ttc tcc tgc atg    960
Arg Val Asp Ala Glu Asp Trp Lys Gln Gly Asp Thr Phe Ser Cys Met
305                 310                 315                 320 gta gga cac gag gct cta cct ctt gcc ttc acc cag aag acc atc gac   1008
Val Gly His Glu Ala Leu Pro Leu Ala Phe Thr Gln Lys Thr Ile Asp
                325                 330                 335 cgc ctt gcg ggt aaa ccc acc cac gtc aac gtg tca gtt gtc atg gcg   1056
Arg Leu Ala Gly Lys Pro Thr His Val Asn Val Ser Val Val Met Ala
            340                 345                 350 gag gca gaa ggc ata tgc tac aaa gac gag ctt taa                   1092
Glu Ala Glu Gly Ile Cys Tyr Lys Asp Glu Leu
        355                 360

<210> SEQ ID NO 8
<211> LENGTH: 363
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Gln Glu Ser Gly Gly Gly Leu Val Gln Ala Gly Gly
1               5                   10                  15

Ser Leu Arg Leu Ser Cys Ala Ala Ser Gly Leu Thr Phe Asp Thr Tyr
            20                  25                  30

Ala Met Gly Trp Phe Arg Gln Ala Pro Gly Lys Lys Arg Glu Tyr Val
        35                  40                  45

Ala Ala Ile Ser Trp Thr Gly Ile Ser Thr Tyr Tyr Ala Asp Ile Ala
    50                  55                  60

Lys Gly Arg Phe Thr Ile Ser Arg Asp Asn Ala Lys Asn Thr Leu Tyr
65                  70                  75                  80

Leu Gln Met Asp Ser Leu Lys Pro Glu Asp Thr Ala Val Tyr Tyr Cys
                85                  90                  95

Ala Ala Gln Arg Ser Leu Asn Val Pro Ala Pro Trp Asp Tyr Trp Gly
            100                 105                 110

Gln Gly Thr Gln Val Thr Val Ser Asp Pro Cys Pro Gln Cys Cys
        115                 120                 125

Lys Pro Ser Leu Ser Leu Gln Pro Pro Ala Leu Ala Asp Leu Leu Leu
    130                 135                 140

Gly Ser Asn Ala Ser Leu Thr Cys Thr Leu Ser Gly Leu Lys Lys Ser
145                 150                 155                 160

Glu Gly Val Ser Phe Thr Trp Gln Pro Ser Gly Gly Lys Asp Ala Val
                165                 170                 175

Gln Ala Ser Pro Thr Arg Asp Ser Cys Gly Cys Tyr Ser Val Ser Ser
            180                 185                 190

Ile Leu Pro Gly Cys Ala Asp Pro Trp Asn Lys Gly Glu Thr Phe Ser
        195                 200                 205

Cys Thr Ala Ala His Ser Glu Leu Lys Ser Ala Leu Thr Ala Thr Ile
    210                 215                 220
```

```
Thr Lys Pro Lys Val Asn Thr Phe Arg Pro Gln Val His Leu Leu Pro
225                 230                 235                 240

Pro Pro Ser Glu Glu Leu Ala Leu Asn Glu Leu Val Thr Leu Thr Cys
                245                 250                 255

Leu Val Arg Gly Phe Ser Pro Lys Asp Val Leu Val Arg Trp Leu Gln
            260                 265                 270

Gly Gly Gln Glu Leu Pro Arg Asp Lys Tyr Leu Val Trp Glu Ser Leu
        275                 280                 285

Pro Glu Pro Gly Gln Ala Ile Pro Thr Tyr Ala Val Thr Ser Val Leu
    290                 295                 300

Arg Val Asp Ala Glu Asp Trp Lys Gln Gly Asp Thr Phe Ser Cys Met
305                 310                 315                 320

Val Gly His Glu Ala Leu Pro Leu Ala Phe Thr Gln Lys Thr Ile Asp
                325                 330                 335

Arg Leu Ala Gly Lys Pro Thr His Val Asn Val Ser Val Val Met Ala
            340                 345                 350

Glu Ala Glu Gly Ile Cys Tyr Lys Asp Glu Leu
        355                 360

<210> SEQ ID NO 9
<211> LENGTH: 423
<212> TYPE: DNA
<213> ORGANISM: Artificial Sequence
<220> FEATURE:
<223> OTHER INFORMATION: J chain

<400> SEQUENCE: 9
caggatgaag aagaaagtac cgtccttgtt gataacaaat gcaagtgcgc ccgtataact      60
tccaggatca tccgctctgc tgaagaccct tcacaagaca ttgtagagag aaacatcaga     120
attattgttc ctctcaacaa cagggagaac atcagcgatc ccacctcacc actccgaacc     180
aatttcgtgt accatttgag cgacctctgt aagaaatgcg atcttacaga agttgagctc     240
gataatcaaa tcgttactgc aacccagagc aacctatgtg atgacgacat tgagacctgc     300
tacgcttacg acagaaacaa gtgctacaca aacacggtcc cattcactta cgatggacag     360
accaaaatgg tgcaaacagc cttgaccccg gattcctgct atcctgacaa agacgagctt     420
taa                                                                   423

<210> SEQ ID NO 10
<211> LENGTH: 1752
<212> TYPE: DNA
<213> ORGANISM: Artificial Sequence
<220> FEATURE:
<223> OTHER INFORMATION: Secretory component

<400> SEQUENCE: 10
aaaagtccca tattcggtcc ccaggatgtt agcagcgttg aaggtagctc agtgtccatc      60
agatgctact acccagccac ctccgtcaac cgtcattctc gtaaatactg gtgccgaata     120
ggagccaaag gccgctgcac aacgctcatc tcctcagagg gttacatctc caaggattac     180
aaaggcagag ccaacctcac caacttccca gagaacggca ccttcgtgat ggatattggt     240
cacttgacgc gcggtgattc tggactctac aaatgtggtc tcggcattag cagccgaggt     300
ctctctttcg atgtttcact cgaggtctca caaggtcctg gacagatagg tgatgtccac     360
gtctacacag cagatttggg ttcaacagta accatcaact gcccctttca atctgagaat     420
gctcagaagc caaaatccgt ttacaaaaaa tgggccagag ccgcgtcct cgtcatcgat     480
```

```
tccaatgggt atttgaacaa caactttacc aacagagcac atctcagtat tcagggtacc    540
aaccaattag tattcagctt cgtcatcaac cgaatccagc tccgcgatgc tggaatatac    600
atctgccagg ctggagatga agagagcagc gctgacctcc aagttttgaa gcccgaacct    660
gaacttattt atgagaccta gggggctca gttacatttg actgcgccct tggccaggaa    720
atggcaaatg ttgccaaatt cctttgccaa ctaaaaaacg gaaaaacctg caatgttgtc    780
atcaacaccc ttggaaagaa ggctcaggac ttcgaaggca ggatccttct cactcccaag    840
gaaaacagcc acttcagcgt tcacatcacg ggacttcgta agaagacgc aggacactac    900
ctttgcggag cccacccctga cggtgagcct aaggaaggct ggccagtcca ggcttggcag    960
ctcttcatca acgaagatac tatgattccc ccaagatcct ccgttgtgag aggtgttgtg   1020
ggaggctccg tggccgtgac ctgccccta acccgaagg aaacaaacag cctgaagtac   1080
tggtgtcgct gggaagagaa tgaaaacggt cgctgcccgc aacttgttga aagcagcggg   1140
ctagttaacg agcaatacga gggtagactc gcgctctacg aggagccagg caacggtacc   1200
ttcacggtca tactcaacca actcaccaac agagacgccg gcttctactg gtgtttgacc   1260
aacgaggact ctcgctggag gtccacggta gaactcaaga ttgttgaagg agaaccgaac   1320
ctcaagctac ccgagaacgt caccgcttgg gttggagaaa ccctcaagct ctcctgccac   1380
ttcccatgca aattctactc ctaccaaaag tactggtgta agtggagcaa caccggttgc   1440
agggcccttc ccagccaaga cgaaggtcaa agccaagcct ttgttaactg tgacaagaag   1500
agccaaatca tctccttgaa cttgaaccct gtcagaaagg aggatgaagg ctggtactgg   1560
tgcggggtga aggacggact ccactatgga gagactgggg ctgtctacgt ggcagtggaa   1620
cagaaggcaa aggggtcagg agatgcccgt ctagcaaacg ctgctcctgc tcctgctgaa   1680
gacgcaatag agccaaggc cagggagact gagaacgagg tcctcttgga tcccagcaaa   1740
gacgagcttt aa                                                        1752

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gtgccttggg tgagaggtta                                                  20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
cactctgccg ttctctttcc                                                  20
```